United States Patent
Holub et al.

(10) Patent No.: US 11,517,239 B2
(45) Date of Patent: Dec. 6, 2022

(54) SYSTEMS AND METHODS FOR PROCESSING AND DISPLAYING ELECTROMYOGRAPHIC SIGNALS

(71) Applicant: Cadwell Laboratories, Inc., Kennewick, WA (US)

(72) Inventors: Michal Holub, Block (SG); David Jensen, Richland, WA (US); Craig Cooper, Pasco, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 818 days.

(21) Appl. No.: 16/375,652

(22) Filed: Apr. 4, 2019

(65) Prior Publication Data

US 2019/0307355 A1 Oct. 10, 2019

Related U.S. Application Data

(60) Provisional application No. 62/653,395, filed on Apr. 5, 2018.

(51) Int. Cl.
| | |
|---|---|
| *A61B 5/296* | (2021.01) |
| *A61B 5/00* | (2006.01) |
| *A61B 5/30* | (2021.01) |
| *A61B 5/316* | (2021.01) |

(52) U.S. Cl.
CPC ............ *A61B 5/296* (2021.01); *A61B 5/30* (2021.01); *A61B 5/316* (2021.01); *A61B 5/7435* (2013.01)

(58) Field of Classification Search
CPC ........... A61B 5/296; A61B 5/30; A61B 5/316; A61B 5/7435; A61B 5/389; A61B 5/7221

USPC ..................................................... 600/546
See application file for complete search history.

(56) References Cited

U.S. PATENT DOCUMENTS

| | | |
|---|---|---|
| 751,475 A | 2/1904 | De Vilbiss |
| 2,320,709 A | 6/1943 | Arnesen |
| 2,807,259 A | 9/1957 | Federico |
| 2,950,437 A | 8/1960 | Stahl |
| 3,165,340 A | 1/1965 | Kuehl |
| 3,659,250 A | 4/1972 | Horton |
| 3,682,162 A | 8/1972 | Colyer |

(Continued)

FOREIGN PATENT DOCUMENTS

| | | |
|---|---|---|
| CN | 104766176 A | 7/2015 |
| DE | 102014008684 A1 | 1/2016 |

(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.

(Continued)

*Primary Examiner* — Jacqueline Cheng
*Assistant Examiner* — Tho Q Tran
(74) *Attorney, Agent, or Firm* — Novel IP

(57) ABSTRACT

The present specification describes systems and methods that enable the automatic detection, analysis and calculation of various processes and parameters associated with electromyography. The methods of the present specification include the automated modulation of analytical or recording states based on the nature of the signal, optimal reference fiber selection, modulating a trigger level, and determining firing parameters.

17 Claims, 12 Drawing Sheets

(56) References Cited

U.S. PATENT DOCUMENTS

| | | |
|---|---|---|
| 3,985,125 A | 10/1976 | Rose |
| 3,993,859 A | 11/1976 | McNeel |
| 4,155,353 A | 5/1979 | Rea |
| 4,262,306 A | 4/1981 | Renner |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |
| 4,705,049 A | 11/1987 | John |
| 4,716,901 A | 1/1988 | Jackson |
| 4,743,959 A | 5/1988 | Frederiksen |
| 4,765,311 A | 8/1988 | Kulik |
| 4,817,587 A | 4/1989 | Janese |
| 4,862,891 A | 9/1989 | Smith |
| 4,889,502 A | 12/1989 | Althouse |
| 4,914,508 A | 4/1990 | Music |
| 5,107,845 A | 4/1992 | Guern |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,438,989 A | 8/1995 | Hochman |
| 5,462,448 A | 10/1995 | Kida |
| 5,472,426 A | 12/1995 | Bonati |
| 5,474,558 A | 12/1995 | Neubardt |
| 5,540,235 A | 7/1996 | Wilson |
| 5,544,286 A | 8/1996 | Laney |
| 5,560,372 A | 10/1996 | Cory |
| 5,565,779 A | 10/1996 | Arakawa |
| 5,578,060 A | 11/1996 | Pohl |
| 5,601,608 A | 2/1997 | Mouchawar |
| 5,602,585 A | 2/1997 | Dickinson |
| 5,625,759 A | 4/1997 | Freeman |
| 5,648,815 A | 7/1997 | Toba |
| 5,664,029 A | 9/1997 | Callahan |
| 5,681,265 A | 10/1997 | Maeda |
| 5,684,887 A | 11/1997 | Lee |
| 5,728,046 A | 3/1998 | Mayer |
| 5,741,261 A | 4/1998 | Moskovitz |
| 5,766,133 A | 6/1998 | Faisandier |
| 5,772,661 A | 6/1998 | Michelson |
| 5,775,331 A | 7/1998 | Raymond |
| 5,775,931 A | 7/1998 | Jones |
| 5,785,648 A | 7/1998 | Min |
| 5,792,044 A | 8/1998 | Foley |
| 5,795,291 A | 8/1998 | Koros |
| 5,830,150 A | 11/1998 | Palmer |
| 5,847,755 A | 12/1998 | Wixson |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,930,379 A | 7/1999 | Rehg |
| 5,931,777 A | 8/1999 | Sava |
| 5,933,929 A | 8/1999 | Kawakami |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,026,180 A | 2/2000 | Wittenstein |
| 6,042,540 A | 3/2000 | Johnston |
| 6,062,216 A | 5/2000 | Corn |
| 6,074,343 A | 6/2000 | Nathanson |
| 6,088,878 A | 7/2000 | Antonucci |
| 6,095,987 A | 8/2000 | Shmulewitz |
| 6,109,948 A | 8/2000 | Kuo |
| 6,116,941 A | 9/2000 | Kuo |
| 6,119,306 A | 9/2000 | Antonucci |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,200,331 B1 | 3/2001 | Swartz |
| 6,206,826 B1 | 3/2001 | Mathews |
| 6,210,202 B1 | 4/2001 | Kuo |
| 6,224,545 B1 | 5/2001 | Cocchia |
| 6,236,874 B1 | 5/2001 | Devlin |
| 6,241,548 B1 | 6/2001 | Kuo |
| 6,259,945 B1 | 7/2001 | Epstein |
| 6,264,491 B1 | 7/2001 | Lord |
| 6,266,558 B1 | 7/2001 | Gozani |
| 6,273,740 B1 | 8/2001 | Lord |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,373,890 B1 | 4/2002 | Freeman |
| 6,425,859 B1 | 7/2002 | Foley |
| 6,450,952 B1 | 9/2002 | Rioux |
| 6,466,817 B1 | 10/2002 | Kaula |
| 6,473,639 B1 | 10/2002 | Fischell |
| 6,500,128 B2 | 12/2002 | Marino |
| 6,535,759 B1 | 3/2003 | Epstein |
| 6,579,114 B2 | 6/2003 | Lord |
| 6,609,018 B2 | 8/2003 | Cory |
| 6,712,795 B1 | 3/2004 | Cohen |
| 6,799,931 B2 | 10/2004 | Kwilosz |
| 6,805,668 B1 | 10/2004 | Cadwell |
| 6,837,716 B1 | 1/2005 | Brazas |
| 6,847,849 B2 | 1/2005 | Mamo |
| 6,851,430 B2 | 2/2005 | Tsou |
| 6,869,301 B2 | 3/2005 | Shimizu |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,104,965 B1 | 9/2006 | Jiang |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B2 | 5/2008 | Jepsen |
| 7,470,236 B1 | 12/2008 | Kelleher |
| 7,522,953 B2 | 4/2009 | Kaula |
| 7,713,210 B2 | 5/2010 | Byrd |
| 7,801,601 B2 | 9/2010 | Maschino |
| 7,914,350 B1 | 3/2011 | Bozich |
| 7,963,927 B2 | 6/2011 | Kelleher |
| 7,983,761 B2 | 7/2011 | Giuntoli |
| 8,147,421 B2 | 4/2012 | Farquhar |
| 8,160,694 B2 | 4/2012 | Salmon |
| 8,192,437 B2 | 6/2012 | Simonson |
| D670,656 S | 11/2012 | Jepsen |
| 8,323,208 B2 | 12/2012 | Davis |
| 8,439,703 B2 | 5/2013 | Natoli |
| 8,876,813 B2 | 11/2014 | Min |
| 8,942,797 B2 | 1/2015 | Bartol |
| 8,958,869 B2 | 2/2015 | Kelleher |
| 9,084,551 B2 | 7/2015 | Brunnett |
| 9,138,586 B2 | 9/2015 | Eiger |
| 9,155,503 B2 | 10/2015 | Cadwell |
| 9,295,401 B2 | 3/2016 | Cadwell |
| 9,352,153 B2 | 5/2016 | Van Dijk |
| 9,730,634 B2 | 8/2017 | Cadwell |
| 10,238,467 B2 | 3/2019 | Cadwell |
| 2001/0049510 A1* | 12/2001 | Burr ............. A61B 5/489 604/272 |
| 2002/0007188 A1 | 1/2002 | Arambula |
| 2002/0009916 A1 | 1/2002 | Lord |
| 2002/0088098 A1 | 7/2002 | Bouley |
| 2002/0095080 A1 | 7/2002 | Cory |
| 2003/0045808 A1 | 3/2003 | Kaula |
| 2003/0074033 A1 | 4/2003 | Pless |
| 2004/0030258 A1 | 2/2004 | Williams |
| 2004/0127810 A1 | 7/2004 | Sackellares |
| 2004/0192100 A1 | 9/2004 | Shimizu |

(56) References Cited

U.S. PATENT DOCUMENTS

| | | |
|---|---|---|
| 2005/0003682 A1 | 1/2005 | Brazas |
| 2005/0075578 A1 | 4/2005 | Gharib |
| 2005/0085743 A1 | 4/2005 | Hacker |
| 2005/0148927 A1* | 7/2005 | Ludin ............... A61M 5/14276 604/66 |
| 2005/0182454 A1 | 8/2005 | Gharib |
| 2005/0182456 A1* | 8/2005 | Ziobro ................. A61N 1/0531 607/48 |
| 2005/0277844 A1* | 12/2005 | Strother ............. A61N 1/37247 600/546 |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |
| 2006/0135877 A1 | 6/2006 | Giftakis |
| 2006/0258951 A1 | 11/2006 | Bleich |
| 2006/0276720 A1* | 12/2006 | McGinnis ............ A61B 5/0006 600/544 |
| 2007/0016097 A1 | 1/2007 | Farquhar |
| 2007/0021682 A1 | 1/2007 | Gharib |
| 2007/0032841 A1 | 2/2007 | Urmey |
| 2007/0046471 A1 | 3/2007 | Nyalamadugu |
| 2007/0049962 A1 | 3/2007 | Marino |
| 2007/0184422 A1 | 8/2007 | Takahashi |
| 2007/0202005 A1 | 8/2007 | Maschke |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0108244 A1 | 5/2008 | Jepsen |
| 2008/0167574 A1 | 7/2008 | Farquhar |
| 2008/0183096 A1 | 7/2008 | Snyder |
| 2008/0194970 A1 | 8/2008 | Steers |
| 2008/0269777 A1 | 10/2008 | Appenrodt |
| 2008/0281313 A1 | 11/2008 | Fagin |
| 2008/0312520 A1 | 12/2008 | Rowlandson |
| 2009/0018399 A1 | 1/2009 | Martinelli |
| 2009/0043221 A1 | 2/2009 | Kaplan |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0196471 A1 | 8/2009 | Goetz |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0113898 A1 | 5/2010 | Kim |
| 2010/0152604 A1 | 6/2010 | Kaula |
| 2010/0168603 A1 | 7/2010 | Himes |
| 2010/0191305 A1 | 7/2010 | Imran |
| 2010/0249638 A1 | 9/2010 | Liley |
| 2010/0286554 A1 | 11/2010 | Davis |
| 2010/0317931 A1 | 12/2010 | Sarkela |
| 2010/0317989 A1 | 12/2010 | Gharib |
| 2011/0082383 A1 | 4/2011 | Cory |
| 2011/0184308 A1 | 7/2011 | Kaula |
| 2011/0295579 A1 | 12/2011 | Tang |
| 2011/0313530 A1 | 12/2011 | Gharib |
| 2012/0003862 A1 | 1/2012 | Newman |
| 2012/0046531 A1 | 2/2012 | Hua |
| 2012/0071779 A1 | 3/2012 | Sarkela |
| 2012/0109000 A1 | 5/2012 | Kaula |
| 2012/0109004 A1 | 5/2012 | Cadwell |
| 2012/0209082 A1 | 8/2012 | Al-Ali |
| 2012/0209346 A1 | 8/2012 | Bikson |
| 2012/0220891 A1 | 8/2012 | Kaula |
| 2012/0238855 A1 | 9/2012 | Lanning |
| 2012/0238893 A1 | 9/2012 | Farquhar |
| 2012/0265040 A1 | 10/2012 | Ito |
| 2012/0296230 A1 | 11/2012 | Davis |
| 2013/0012880 A1 | 1/2013 | Blomquist |
| 2013/0109996 A1 | 5/2013 | Turnbull |
| 2013/0138010 A1 | 5/2013 | Nierenberg |
| 2013/0152657 A1 | 6/2013 | Swinehart |
| 2013/0204315 A1 | 8/2013 | Wongsarnpigoon |
| 2013/0253447 A1* | 9/2013 | Ball ..................... A61M 5/46 604/272 |
| 2013/0304407 A1 | 11/2013 | George |
| 2014/0121555 A1 | 5/2014 | Scott |
| 2014/0275926 A1 | 9/2014 | Scott |
| 2014/0276181 A1 | 9/2014 | Sun |
| 2015/0150512 A1* | 6/2015 | Warner .................. A61B 5/24 600/300 |
| 2015/0230749 A1 | 8/2015 | Gharib |
| 2015/0238106 A1 | 8/2015 | Lappalainen |
| 2015/0351643 A1 | 12/2015 | Edwards |
| 2015/0372433 A1 | 12/2015 | Lisogurski |
| 2016/0000382 A1 | 1/2016 | Jain |
| 2016/0174861 A1 | 6/2016 | Cadwell |
| 2016/0270679 A1* | 9/2016 | Mahon ................ A61B 5/7246 |
| 2016/0328991 A1 | 11/2016 | Simpson |
| 2017/0056663 A1 | 3/2017 | Kaemmerer |
| 2017/0100047 A1* | 4/2017 | Edwards ............. A61B 5/0022 |
| 2018/0117309 A1 | 5/2018 | Rapoport |
| 2018/0140829 A1 | 5/2018 | Ramos De Miguel, Sr. |
| 2018/0161123 A1 | 6/2018 | Cadwell |
| 2018/0198218 A1 | 7/2018 | Regan |
| 2018/0256097 A1 | 9/2018 | Bray |
| 2018/0296277 A1 | 10/2018 | Schwartz |
| 2019/0190187 A1 | 6/2019 | Fukazawa |
| 2020/0022603 A1* | 1/2020 | Cardenas .............. A61B 5/316 |
| 2020/0108246 A1 | 4/2020 | Cadwell |
| 2020/0297282 A1 | 9/2020 | Batzer |
| 2020/0330772 A1 | 10/2020 | Hartmann-Bax |

FOREIGN PATENT DOCUMENTS

| | | | |
|---|---|---|---|
| EP | 298268 | | 1/1989 |
| EP | 0863719 | A1 | 9/1998 |
| EP | 890341 | | 1/1999 |
| EP | 972538 | | 1/2000 |
| EP | 1182965 | B1 | 3/2002 |
| EP | 2173238 | A2 | 4/2010 |
| JP | H11513592 | A | 11/1999 |
| JP | 2008546509 | A | 12/2008 |
| WO | 2000038574 | A1 | 7/2000 |
| WO | 2000066217 | A1 | 11/2000 |
| WO | 2001037728 | A1 | 5/2001 |
| WO | 2003005887 | A2 | 1/2003 |
| WO | 2005030318 | A1 | 4/2005 |
| WO | 2006042241 | A2 | 4/2006 |
| WO | 2016028822 | A1 | 2/2016 |
| WO | WO2016105571 | A1 * | 6/2016 ........... A61B 5/0488 |

OTHER PUBLICATIONS

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12):1375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

(56) References Cited

OTHER PUBLICATIONS

H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18(8):626-631 (1996).
Bergey et al., "Endoscopic Lateral Transpsoas Approach to the Lumbar Spine", Spine 29(15):1681-1688 (2004).
Holland, "Spine Update, Intraoperative Electromyography During Thoracolumbar Spinal Surgery", 23(17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. 1-31 Mar. 20, 1998, The Magstim Company Limited.
Kevin T. Foley, et. al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et. al., "Minimally Invasive Vertebral Replacement with Cages in Thoracic and Lumbar Spine", European Journal of Trauma, 2001, No. 6, pp. 292-300.
Lenke, et. al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et. al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12(2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et. al., "The NerveSeeker: A System for Automated Nerve Localization", Regional Anesthesia 17:151-162 (1992).
Reidy, et. al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et. al., "The usefulness of Electrical Stimulation for Assessing Pedicle Screw Placements", Journal of Spinal Disorders, 13 (4):283-289 (2000).
U.Schick, et. al., "Microendoscopic lumbar discectomy versus open surgery: an intraoperative EMG study", pp. 20-26, Published online: Jul. 31, 2001 © Springer-Verlag 2001.
Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapter 3, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al, Electrical characteristics of peripheral nerve stimulators, implications for nerve localization, Dept. of Anesthesia, University of Cincinnati College of Medicine, Cincinnati, OH 45267, pp. 73-77.
Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.compumedics.com.au/wp-content/uploads/2016/08/AD125-02-Profusion-EEG4-brochureLR.pdf (Year:2017).
Intelimed Website, "Compumedics Profusion EEG 5 Top Features" accessed online Oct. 9, 2021, available online Sep. 30, 2014 2014).
Deff Corporation, No more confusion about which direction to plug in. A USB cable that can be plugged in both ways is now available. A connector is equipped with an LED indicator to check a charging status of a smartphone. Nov. 6, 2015 (Dec. 28, 2021 Search) Internet URL:https://deff.co.jp/news/dca-mbled (Document showing known technology).
"Long, S; "Phase Locked Loop Circuits", Apr. 27, 2005". (Year: 2005).
Brainstorm website, https://web.archive.org/web/20180421074035/https://neuroimage.usc.edu/brainstorm/Tutorials/MontageEditor, available online Apr. 21, 2018 (Year: 2018).

(56) References Cited

OTHER PUBLICATIONS

Brainstorm website, https://web.archive.org/web/20180330235454/http://neuroimage.usc.edu/brainstorm/Tutorials/CreateProtocol,) available on Mar. 30, 2018 (Year: 2018).
Brainstorm website,https://web.archive.org/web/20180416072211/http://neuroimage.usc.edu/brainstorm/Screenshots ,available on Apr. 16, 2018 (Year: 2018).
Brainstorm website,https://web.archive.org/web/20180411211909/https://neuroimage.usc.edu/brainstorm/Introduction,available on Apr. 11, 2018 (Year: 2018).
Brainstorm website,https://web.archive.org/web/20180505021718/https://neuroimage.usc.edu/brainstorm/Tutorials/Epileptogenicity, available on May 5, 2018 (Year: 2018).

* cited by examiner

SYSTEMS AND METHODS FOR PROCESSING AND DISPLAYING ELECTROMYOGRAPHIC SIGNALS

CROSS-REFERENCE

The present application relies on U.S. Provisional Patent Application No. 62/653,395, entitled "Systems and Methods for Processing and Displaying Electromyographic Signals" and filed on Apr. 5, 2018, for priority, which is incorporated herein by reference in its entirety.

FIELD

The present specification is related generally to the field of electromyography (EMG). More specifically the present specification is related to systems and methods for enabling automatic detection, display and analysis of a plurality of processes and parameters associated with EMG signals or data.

BACKGROUND

Electromyography (EMG) is an electrodiagnostic technique for evaluating and recording the electrical activity produced by skeletal muscles. An electromyograph detects the electric action potential generated by muscle cells when these cells are electrically or neurologically activated. The signals can be analyzed to detect medical abnormalities, activation level, recruitment order, and/or for analysis of the biomechanics of human or animal movement. An EMG electrode, sensor, or probe, such as a monopolar or concentric EMG needle, is used as a diagnostic tool for assessing, analyzing, diagnosing, and recording electrical activity occurring in the tissues and muscles. The determined quality and/or status of the neuromuscular and tissue dynamics aid in the diagnosis and/or treatment of conditions associated with said tissues and/or muscles.

While performing an EMG examination, an operator needs to actively switch between a first task of interacting, viewing, manually calculating and interpreting EMG signals associated with a plurality of motor units as displayed on a monitor of an EMG machine and a second task of attending to a patient who is undergoing a rather not so soporific EMG examination. EMG display and analysis software is conventionally utilized to record, display and analyze motor unit signals. However, the present EMG software tools still require manual intervention and a dependency on the ability of the operator to interpret the EMG signals thereby adding human interpretation, subjectivity, and a potential for errors to an already arduous manual task.

Thus, there is a need for systems and methods that enable automatic detection, analysis and calculation of a plurality of processes and parameters associated with EMG, MUPs (Motor Unit Potential), MUPT (Motor Unit Potential Train), and muscle fiber signals or data.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a method of using an electromyography device to automatically set a recordation and/or analytical state of a motor unit, the method comprising: using the electromyography device, generating an EMG signal from a needle electrode positioned in the patient's muscle tissues; using the electromyography device, determining if the EMG signal corresponds to one of a plurality of predefined artifacts; using the electromyography device, automatically setting the recordation and/or analytical state to a first status if the EMG signal is determined to be at least one of the plurality of predefined artifacts; and using the electromyography device, automatically setting the recordation and/or analytical state to a second status if the EMG signal is determined to not be one of the plurality of predefined artifacts.

Optionally, the first status corresponds to stopping the recordation or analysis of the EMG signal corresponding to the motor unit and wherein the second status corresponds to recording or analyzing the EMG signal corresponding to the motor unit.

Optionally, the method further comprises using the electromyography device to identify an excessive contraction of the muscle tissues based on whether a number of peaks per second detected in the EMG signal is greater than a threshold number of peaks per second, wherein a first of the plurality of predefined artifacts is associated with the excessive contraction of the muscle tissues. Optionally, the threshold number of peaks per second ranges between 50 and 60 peaks per second.

Optionally, the method further comprises using the electromyography device to identify a second of the plurality of predefined artifacts based on whether the EMG signal comprises a mains noise frequency. Optionally, the mains noise frequency is in a range from at least one of 50 Hz to 55 Hz or 55 Hz to 65 Hz. Optionally, the second of the plurality of predefined artifacts is associated with a needle electrode not being properly inserted into the muscle tissues.

Optionally, the method further comprises using the electromyography device to identify a presence of a predefined waveform in the EMG signal, wherein the predefined waveform comprises a first portion having a first amplitude and a first frequency and a second portion having a second amplitude and a second frequency, wherein the first amplitude is greater than the second amplitude, wherein the first frequency is greater than the second frequency, and wherein the second portion precedes or follows the first portion. Optionally, the first portion defines a burst having a duration of less than 50 milliseconds. Optionally, the first amplitude has an amplitude of greater than 500 µV. Optionally, a third of the plurality of predefined artifacts is associated with a movement of a needle electrode from a first site to a second site in the muscle tissues.

The present specification also discloses an electromyography device having a non-transient memory and a processor configured to execute a plurality of programmatic instructions stored in the non-transient memory, wherein, upon execution of the plurality of programmatic instructions, the electromyography device: generate an EMG signal while sampling a patient's muscle tissues via a needle electrode; determine if the EMG signal corresponds to one of a plurality of predefined artifacts; automatically set a recordation and/or analytical state to a first status if the EMG signal is determined to be at least one of the plurality of predefined artifacts; and automatically set the recordation and/or analytical state to a second status if the EMG signal is determined to not be one of the plurality of predefined artifacts.

Optionally, the first status corresponds to stopping the recordation or analysis of the EMG signal and wherein the second status corresponds to recording or analyzing the EMG signal.

Optionally, the electromyograph device is further configured to identify an excessive contraction of the muscle tissues based on whether a number of peaks per second detected in the EMG signal is greater than a threshold number of peaks per second, wherein a first of the plurality of predefined artifacts is associated with the excessive contraction of the muscle tissues. Optionally, the threshold number of peaks per second ranges between 50 and 60 peaks per second.

Optionally, the electromyograph device is further configured to identify a second of the plurality of predefined artifacts based on whether the EMG signal comprises a mains noise frequency. Optionally, the mains noise frequency is in a range from at least one of 50 Hz to 55 Hz or 55 Hz to 65 Hz. Optionally, the second of the plurality of predefined artifacts is associated with a needle electrode not being properly inserted into the muscle tissues.

Optionally, the electromyograph device is further configured to identify a presence of a predefined waveform in the EMG signal, wherein the predefined waveform comprises a first portion having a first amplitude and a first frequency and a second portion having a second amplitude and a second frequency, wherein the first amplitude is greater than the second amplitude, wherein the first frequency is greater than the second frequency, and wherein the second portion precedes or follows the first portion. Optionally, the first portion defines a burst having a duration of less than 50 milliseconds. Optionally, a third of the plurality of predefined artifacts is associated with a movement of a needle electrode from a first site to a second site in the muscle tissues.

The present specification also discloses a method of using an electromyography device to automatically select an optimal reference muscle fiber of a plurality of muscle fibers in a patient's muscle, the method comprising: using the electromyography device, recording an EMG signal from the plurality of muscle fibers wherein the EMG signal is generated from a needle electrode positioned within a motor unit of the patient's muscle, wherein the motor unit is in electrical communication with the plurality of muscle fibers; using the electromyography device, determining if the plurality of muscle fibers comprise more than two muscle fibers; using the electromyography device and based on whether the plurality of muscle fibers comprise more than two muscle fibers and iterating through each of the plurality of muscle fibers by selecting each of the plurality of muscle fibers as a reference fiber and determining a corresponding jitter value for each of the plurality of muscle fibers to thereby generate a set of corresponding jitter values; using the electromyography device, identifying a minimum jitter value from the set of corresponding jitter values; and using the electromyography device, selecting an optimal reference fiber corresponding to the identified minimum jitter value.

Optionally, the method further comprises, using the electromyography device, to determine a minimum jitter value without first selecting one of the plurality of muscle fibers as a reference fiber if the plurality of muscle fibers does not comprise more than two muscle fibers.

The present specification also discloses an electromyography device having a non-transient memory and a processor configured to execute a plurality of programmatic instructions stored in the non-transient memory, wherein, upon execution of the plurality of programmatic instructions, the electromyography device: records an EMG signal from a plurality of muscle fibers of a patient; determines if the plurality of muscle fibers comprise more than two muscle fibers; based on whether the plurality of muscle fibers comprise more than two muscle fibers, iterate through each of the plurality of muscle fibers by selecting each of the plurality of muscle fibers as a reference fiber and determining a corresponding jitter value for each of the plurality of muscle fibers to thereby generate a set of corresponding jitter values; identify a minimum jitter value from the set of corresponding jitter values; and select an optimal reference fiber corresponding to the identified minimum jitter value.

Optionally, the electromyography device determines a minimum jitter value without first selecting one of the plurality of muscle fibers as a reference fiber if the plurality of muscle fibers does not comprise more than two muscle fibers.

The present specification also discloses a method of using an electromyography device to modulate a trigger level of an EMG signal shown within a graphical user interface rendered in a display of the electromyography device, the method comprising: using an EMG trigger level engine in the electromyography device, determining a highest recurring peak amplitude of the EMG signal and displaying said EMG signal within the graphical user interface; using the EMG trigger level engine, automatically setting a trigger level amplitude at a predetermined value above the highest recurring peak amplitude and displaying the trigger level amplitude relative to a waveform of the EMG signal; using the EMG trigger level engine, automatically displaying, within the graphical user interface, portions of the EMG signal having amplitudes above the trigger level.

Optionally, the predetermined value of the trigger level amplitude is automatically set by the EMG trigger level engine in a range of 50% to 90% of the highest recurring peak amplitude.

Optionally, the method further comprises, using the EMG trigger level engine, changing the predetermined value of the trigger level amplitude to a second value if an average of the highest recurring peak amplitude changes by more than a predefined value over a predefined period of time.

Optionally, the trigger level amplitude is visually displayed as a line superimposed on the waveform of the EMG signal.

The present specification also discloses an electromyography device having a non-transient memory and a processor configured to execute a plurality of programmatic instructions stored in the non-transient memory, wherein, upon execution of the plurality of programmatic instructions, the electromyography device: determines a highest recurring peak amplitude of the EMG signal and displays the EMG signal within the graphical user interface; automatically sets a trigger level amplitude at a predetermined value above the highest recurring peak amplitude and displays the trigger level amplitude relative to a displayed waveform of the EMG signal; and automatically displays, within the graphical user interface, portions of the EMG signal having amplitudes above the trigger level.

Optionally, the predetermined value of the trigger level amplitude is automatically set in a range of 50% to 90% of the highest recurring peak amplitude.

Optionally, the electromyography device is further configured to change the predetermined value of the trigger level amplitude to a second value if an average of the highest recurring peak amplitude changes by more than a predefined amount over a predefined period of time.

Optionally, the trigger level amplitude is visually displayed as a line superimposed on the waveform of the EMG signal.

The present specification also discloses a computer-implemented method for using an electromyography device to determine firing parameters associated with a plurality of EMG signals corresponding to a plurality of motor units and displaying the firing parameters within a graphical user interface rendered in a display of the electromyography device, the method comprising: using the electromyography device, generating the plurality of EMG signals from one or more needle electrodes positioned inside a patient's muscle; using the electromyography device, recording the plurality of EMG signals during a muscle contraction; using the electromyography device, extracting at least one of motor unit potential data or motor unit potential train data from the plurality of EMG signals; using the electromyography device, determining at least one of a recruitment ratio or a recruitment frequency for the plurality of EMG signals; and displaying the at least one recruitment ratio or recruitment frequency within the graphical user interface.

The present specification also discloses an electromyography device having a non-transient memory and a processor configured to execute a plurality of programmatic instructions stored in the non-transient memory, wherein, upon execution of the plurality of programmatic instructions, the electromyography device being configured to determine firing parameters associated with a plurality of EMG signals corresponding to a plurality of motor units and to display the firing parameters within a graphical user interface rendered in a display of the electromyography device, wherein the electromyography device: generates the plurality of EMG signals from one or more needle electrodes positioned inside a patient's muscle; records the plurality of EMG signals during a muscle contraction; extracts at least one of motor unit potential data or motor unit potential train data from the plurality of EMG signals; determines at least one of a recruitment ratio or a recruitment frequency for the plurality of EMG signals; and displays the at least one recruitment ratio or recruitment frequency within the graphical user interface.

The present specification also discloses a method of setting a state of recordation and analysis of motor units, without manual intervention, the method comprising: generating an EMG signal while sampling a patient's muscle tissues using a needle electrode; determining if said EMG signal corresponds to at least one of a first, a second and a third artifact; setting the state to a first status if said EMG signal is determined to be at least one of said first, second or third artifacts; and setting the state to a second status if said EMG signal is determined to not be an artifact.

Optionally, said first status corresponds to stopping motor unit recordation and analysis and wherein said second status corresponds to commencing or continuing motor unit recordation and analysis.

Optionally, said first artifact is associated with an excessive contraction of the muscle tissues, and wherein said excessive contraction is identified if a number of peaks per second detected in said EMG signal is greater than a threshold number of peaks per second.

Optionally, said threshold number of peaks per second ranges between 50 and 60 peaks per second.

Optionally, said second artifact is associated with a condition of the needle electrode not being inserted into the muscle tissues, and wherein the condition is identified if said EMG signal comprises a mains noise frequency.

Optionally, said mains noise frequency ranges between either 45 Hz to 55 Hz or 55 Hz to 65 Hz.

Optionally, said mains noise frequency is 60 Hz.

Optionally, said third artifact is associated with a movement of the needle electrode from a first site to a second site in the muscle tissues, and wherein said movement is identified by a presence of a waveform comprising short, high amplitude bursts preceded and followed by substantially low activity or low amplitude signals.

Optionally, said bursts are of a duration of less than 50 milliseconds.

Optionally, said bursts have an amplitude of 10s of mV.

The present specification also discloses a method of selecting an optimal reference fiber without manual intervention, the method comprising: positioning a needle electrode within a motor unit of a patient's muscle, wherein said motor unit is connected to a plurality of muscle fibers; recording an EMG signal from the plurality of muscle fibers; determining if the plurality of muscle fibers is greater than two fibers; iterating through said plurality of muscle fibers, if the plurality of muscle fibers is greater than two, by selecting each fiber as a reference fiber and calculating a corresponding jitter value thereby generating a plurality of jitter values corresponding to each of said plurality of fibers; and selecting an optimal reference fiber that corresponds to least jitter from said plurality of jitter values.

The present specification also discloses a computer-implemented method for modulating a trigger level within a graphical user interface rendered in a display, said modulation being with reference to each of a plurality of EMG signals associated with a plurality of corresponding motor units firing during an EMG examination and being implemented by an EMG trigger engine in a computer in data communication with the display, the method comprising: determining a highest recurring peak amplitude of a signal, from said plurality of EMG signals, and displaying said signal within said graphical user interface; setting a trigger level amplitude at a predetermined value above said highest recurring peak amplitude and displaying said trigger level amplitude as a line superimposed on the display of said signal; displaying, within said graphical user interface, portions of said signal having amplitudes above said trigger level; and repeating the steps of determining, setting and displaying for each of said plurality of EMG signals.

Optionally, said predetermined value of the trigger level amplitude is set at 80% of the highest recurring peak amplitude.

The present specification also discloses a computer-implemented method for calculating firing parameters associated with a plurality of EMG signals corresponding to a plurality of motor units and displaying said firing parameters within a graphical user interface rendered in a display, said plurality of motor units firing during an EMG examination and said method being implemented by an engine in a computer in data communication with the display, the method comprising: positioning a needle electrode inside a patient's muscle to generate said plurality of EMG signals; recording said plurality of EMG signals during muscle contraction; extracting motor unit potential and motor unit potential train information from said plurality of EMG signals; calculating a recruitment ratio and a recruitment frequency for said plurality of EMG signals; and displaying said recruitment ratio and recruitment frequency within said graphical user interface.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Definitions

Figure 1:
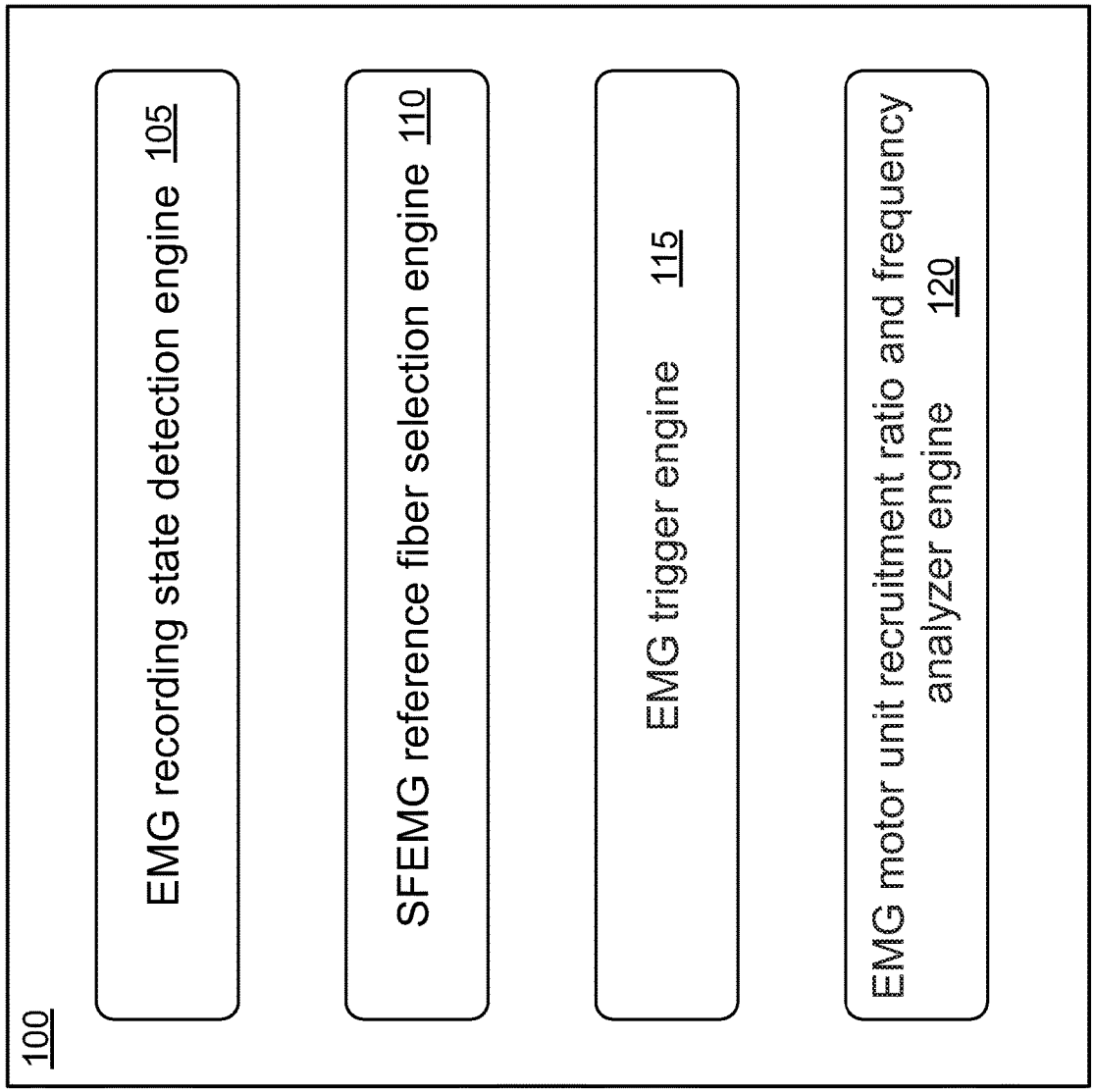
FIG. 1 is a block diagram illustrating a plurality of automation engines integrated within an EMG software application, in accordance with an embodiment of the present specification.

The term "Motor Unit" refers to the smallest functional unit that enables contracting of a muscle. It consists of a single nerve fiber (axon) that connects to (innervates) multiple muscle fibers through a neuro-muscular junction. When a person initiates a voluntary movement, for instance stretching a finger, the desire to move the finger will result in a signal from the motor cortex that will travel through the nerve in the spine and initiate a signal in the peripheral nerve fiber. This signal is then conducted through the axon and transmitted through the neuro-muscular junction to all the muscle fibers innervated by the same nerve fiber—that is, the motor unit. A motor unit can connect to several hundred up to thousands of muscle fibers.

The term "Motor Unit Potential (MUP)" refers to potentials generated by synchronous firing of predefined groups of muscle fibers. The force in a muscle is modulated by modulating the firing rate of an individual motor unit and/or increasing and decreasing the number of simultaneously firing motor units. Therefore it is of clinical interest to access and analyze the configuration/morphology of individual MUPs, the number of concurrently firing MUs, the firing frequency and the frequency variation of a single MU and the configuration and contribution of the individual muscle fibers contributing to a specific MUP.

The term "Motor Unit Potential Train (MUPT)" refers to a train or reoccurring pattering, of electrical activity recorded during an EMG generated by the same motor unit.

The term "Jitter" refers to a variation in timing that is measured in microseconds. Since a plurality of muscle fibers is innervated by a single axon (motor unit) it can be expected that the resulting contraction/signal in each muscle fiber connected to the same motor unit is synchronous with small variation among contractions of the plurality of muscle fibers. The Single Fiber EMG (SFEMG) test is aimed at measuring the variation in timing between different muscle fiber activation in the same motor unit, whereby the variation in timing is known as jitter and is measured in micro seconds (µs). To measure the jitter, one of the muscle fiber signals is selected as a reference fiber against which all the other fibers are measured. A normal variation/jitter ranges typically from 10-30 µs. Increased jitter is a sign of pathology.

The term "firing rate" refers to the rate at which an individual motor unit is firing. Different diseases affect how muscle force is created and manifests itself in the number of motor units, their firing rate, and how new motor units are added as muscle force is increased.

The term "firing pattern" refers to the arrangement of motor units and muscle activity along a set time base in an EMG recording.

The term "Recruitment Ratio" refers to a measurement that takes into consideration both the firing rate as well as the number of concurrently firing motor units into one value and is calculated by taking the highest firing rate of any active motor unit and dividing it by the total number of motor units firing.

The term "Recruitment Frequency" refers to the frequency or rate at which a first motor unit fires before a second motor unit is recruited.

The terms "automation", "automatic" and "automatically" refer to execution of programmatic code or instructions, without human intervention, based solely on an occurrence of one or more predefined events and/or conditions that are measured, monitored, or determined by the execution of programmatic instructions on a computing device.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The "computing device" further comprises at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

An Enhanced EMG Display and Analysis Software

FIG. 1 is a block diagram of an EMG software application comprising a plurality of engines or modules for automatic detection, analysis and display of EMG signals or data, in accordance with an embodiment of the present specification. Referring now to FIG. 1, the EMG software 100 comprises an EMG recording state detection engine 105, an SFEMG reference fiber selection engine 110, an EMG trigger engine 115, and an EMG motor unit recruitment ratio and frequency analyzer engine 120. In embodiments, the EMG software application, with the plurality of automation engines or modules, is executed on a "computing device". Each of these automation engines and their functionality will be discussed in greater detail below.

Automatic EMG Recording State Detection Module 105

During an EMG recording in order to study a patient's neuromuscular condition such as, for example, neuropathy and erratic muscular spasm, muscle activity is examined by inserting a micro-stimulation sensor or probe, such as a needle electrode, (hereinafter referred to as a 'needle') into different sites within a muscle. The needle samples different parts of the muscle when the muscle is in a plurality of states or levels of contraction such as, completely relaxed (recording spontaneous activity), slight contraction force (motor unit analysis), and high level of contraction (looking at interference pattern).

In accordance with embodiments of the present specification, the EMG display and analysis software include an EMG recording state detection engine or module 105 to automatically identify/detect the plurality of muscle states. In some embodiments, the muscle states include, but are not limited to, excessive muscle contraction, needle non-insertion state in a muscle site, and needle movement states.

Excessive muscle contraction, for purposes of the present specification, is defined as muscle contractions creating a level of EMG activity that results in a signal that is not meaningful for analysis. In embodiments of the present specification, excessive muscle contraction is determined by the number of EMG signal peaks per second exceeding a predefined threshold. The higher the muscle contraction level, the more peaks are detected. A peak is when the signal changes direction from upward going to downward going, or vice versa, with a minimum amount of amplitude. In some embodiments, the minimum amplitude is 25 µV. An intensity bar measuring the peaks and amplitude is implemented and displays this information in run-time. In some embodiments, any signal above 50 peaks per second (wherein each of the peaks has an amplitude of at least 25 µV) is considered excessive muscle contraction, or artifact relating to excessive muscle contraction, indicating too much EMG activity that cannot be used for analysis.

Needle non-insertion, for purposes of the present specification, is defined as when the needle for the EMG study is not inserted into a patient's muscle. Regarding needle non-insertion, in embodiments of the present specification, the EMG signal is analyzed for excessive amount of mains content or mains noise, which includes signals having a frequency in the range of 50 Hz-60 Hz. An increased mains content of the EMG signal in comparison to energy outside of this frequency range typically indicates that the needle is not inserted into the patient (into a muscle).

Mains content or mains noise evaluation is performed by applying a mains notch filter and evaluating the energy level in the filtered signal. In some embodiments, mains frequency (50 Hz-60 Hz) exceeding 10% of the total signal energy is indicative of needle non-insertion, or artifact relating to needle non-insertion, and the analysis is stopped.

Needle movement, for purposes of the present specification, is defined as movement of the needle from one site to another while inserted in a patient's muscle or movement of the needle from one muscle to another. In embodiments of the present specification, for needle movement, the EMG signal is analyzed for sudden, high amplitude, and very rapid bursts of activity which are characteristic for movement of the needle. In embodiments, a running average of the ongoing EMG signal is analyzed and, if there is a sudden activity (duration of less than 50 ms) with high amplitude (>500 µV) in an otherwise "quiet" EMG signal (average activity<50 µV), then it is considered to be a needle movement activity, or artifact relating to needle movement.

The EMG recording state detection engine or module 105 automatically identifies/detects these states so as to be able to begin and end recording and differentiate and remove artifacts or spurious signals from an analysis of biologic or clinically relevant EMG activity. The plurality of muscle and needle states are identified/detected automatically in real-time during the EMG recording to substantially reduce interference. In various embodiments, the EMG recording state detection engine or module 105 analyzes different baseline characteristics, such as fullness of the baseline or the amount of activity in the baseline. In some embodiments, baseline fullness or baseline activity is measured by peaks per second (PPS) and a baseline threshold can be set by the end user. In some embodiments, other characteristics, such as baseline instability, are not controlled by the end user but are monitored through software algorithms in the system. The automatic recording on/off switching and detection and removal of artifacts and spurious signals eliminates the need for the end user to manually switch off recording during collection and to subjectively detect and delete affected data after collection.

The EMG recording state detection engine or module 105 implements a plurality of instructions to continuously analyze incoming EMG signals to determine a nature or characteristic of the signals and automatically set a motor unit recording and analysis (EMG or MUP analysis) to an 'on' or 'off' state depending upon the determined nature of the signals. In accordance with an aspect, an objective of determining the nature or characteristic of the signals is to determine if the signals represent artifact data or actual, non-artifact biologic EMG data. The EMG recording state detection engine or module 105 is configured to stop recording and processing of a signal if it represents artifact data or noisy signal acquisition states.

In various embodiments, an incoming EMG signal may be associated with at least one of the following events: needle movement, needle not inserted, relaxed muscle, slight contraction of a muscle, and excessive contraction level of a muscle. A completely relaxed muscle produces an EMG signal that would be 'silent' with virtually no activity. Slight muscle contraction produces an EMG signal represented by only a few motor units firing (1-3) and firing at a low frequency (less than 8-10 Hz). Needle movement, needle non-insertion, and excessive muscle contraction would result in non-meaningful, or artifact signals, as defined above. An EMG signal associated with any of these events is considered an artifact relating to the event and, in some embodiments, recording is then stopped.

The EMG recording state detection engine 105 uses the determined nature of the incoming signal to enable the EMG display and analysis software to automatically exclude artifact data from actual, non-artifact biologic EMG data, thus preventing recordation and analysis of noisy data. In embodiments, artifact data refers to EMG activity associated with at least one of the following events: movement of the needle from one muscle site to another, needle not inserted in the muscle, and excessive contraction level of a muscle, as defined above.

Figure 2A:
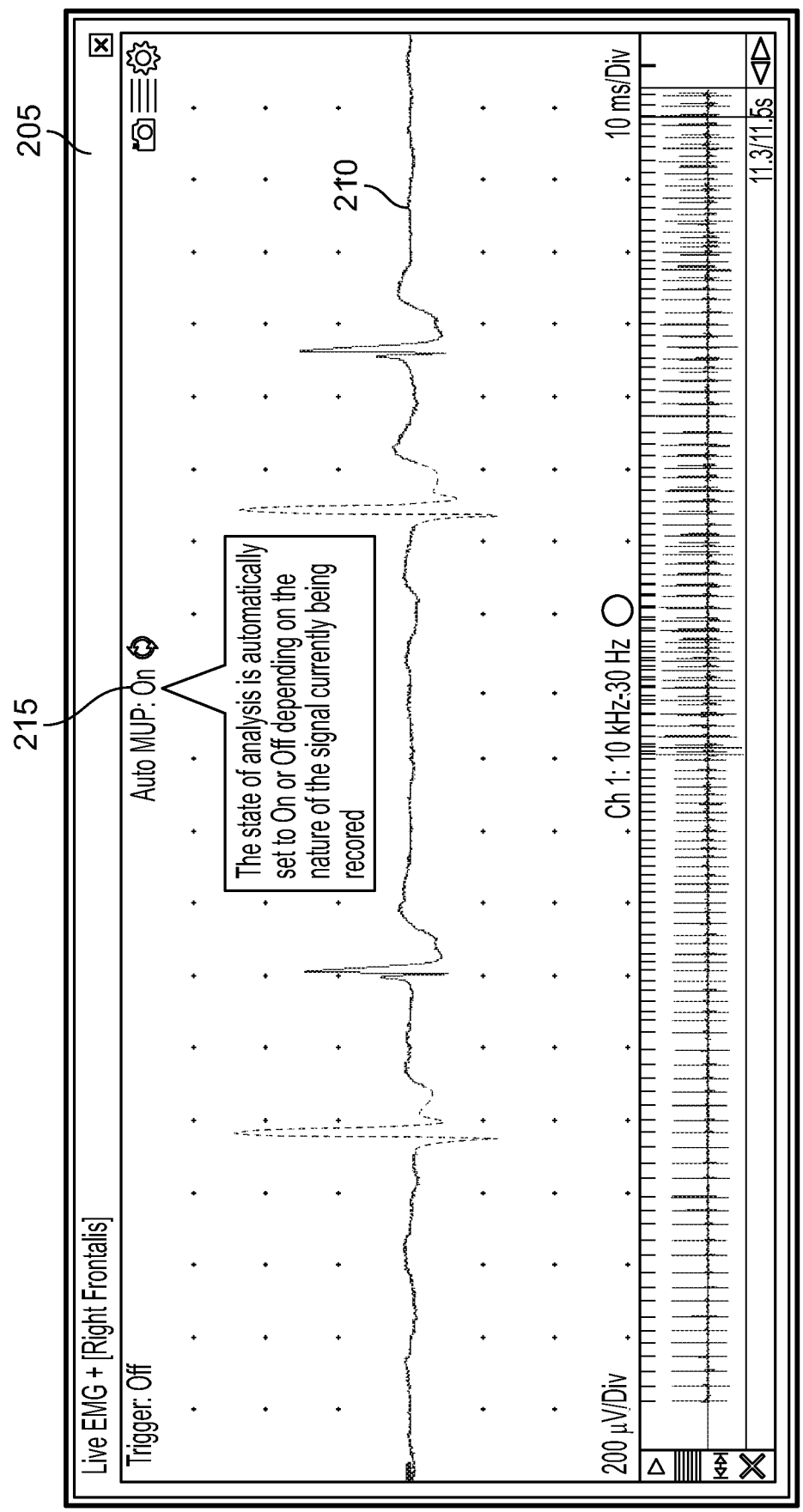
FIG. 2A is an EMG Graphical User Interface (GUI) screen illustrating setting a state of motor unit action potential analysis automatically, in accordance with an embodiment of the present specification.

FIG. 2A is an EMG Graphical User Interface (GUI) screen illustrating setting a state of motor unit potential (MUP) analysis automatically, in accordance with an embodiment of the present specification. In an embodiment, the state of motor unit potential analysis (EMG analysis) is automatically set to 'on' or 'off' depending on the nature of the EMG signal 210 being recorded. The EMG recording and analysis is automatically set to the 'off' state when the EMG recording state detection engine determines that the signal 210 being recorded is an artifact, such as a signal corresponding to movement of the needle from one site of a muscle to another, for example.

When the EMG recording state detection engine determines that the signal 210 being recorded is actual or non-artifact, such as a signal corresponding to slight contraction of the muscle, the EMG recording and analysis is automatically set to the 'on' state. In embodiments, actual or non-artifact EMG signals are considered clinically relevant signals that a clinician or specialist would recognize on manual analysis. These clinically relevant signals are fast signals with sufficiently high amplitudes and are repeated at a reasonably static frequency. The amplitudes which are indicative of clinically relevant signals are dependent on the muscle being studied, since different muscles have unique acceptable amplitude ranges. Accordingly, a clinically relevant signal, or a non-artifact signal, has an amplitude that exceeds a predefined threshold value which is dependent upon the muscle being examined. Similarly, the frequencies which are indicative of clinically relevant signals are dependent on the muscle being studied, since different muscles have unique acceptable frequency ranges. Accordingly, a clinically relevant signal, or a non-artifact signal, has a frequency that is within a predefined range which is dependent upon the muscle being examined. It should be appreciated that turning the analysis on/off automatically not only relieves an operator or physician from having to interact with an EMG machine manually while performing a tedious EMG examination, but also enables avoiding invalid analysis due to a dominance of artifact data.

A displayed visual or auditory indicator 215 conveys if the state of analysis is 'on' or 'off'. In some embodiments, the indicator 215 is an icon that changes color, text, and/or graphical images to indicate 'on' and 'off' states. In some embodiments, the indicator 215 is a text conveying 'on' and 'off' states.

Figure 2B:
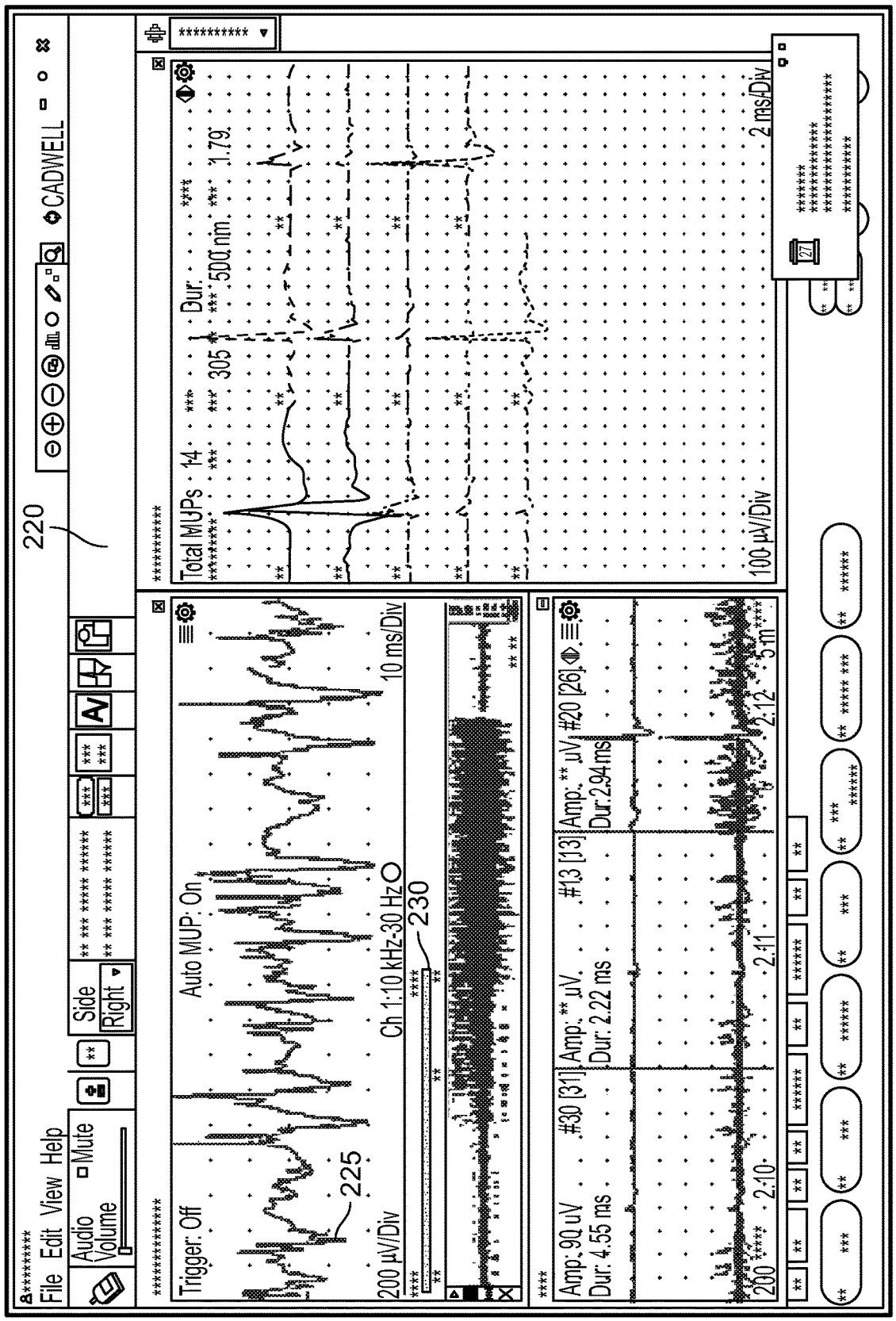
FIG. 2B is an EMG GUI screen illustrating detection of an artifact signal associated with excessive muscle contraction, in accordance with an embodiment of the present specification.
Figure 2C:
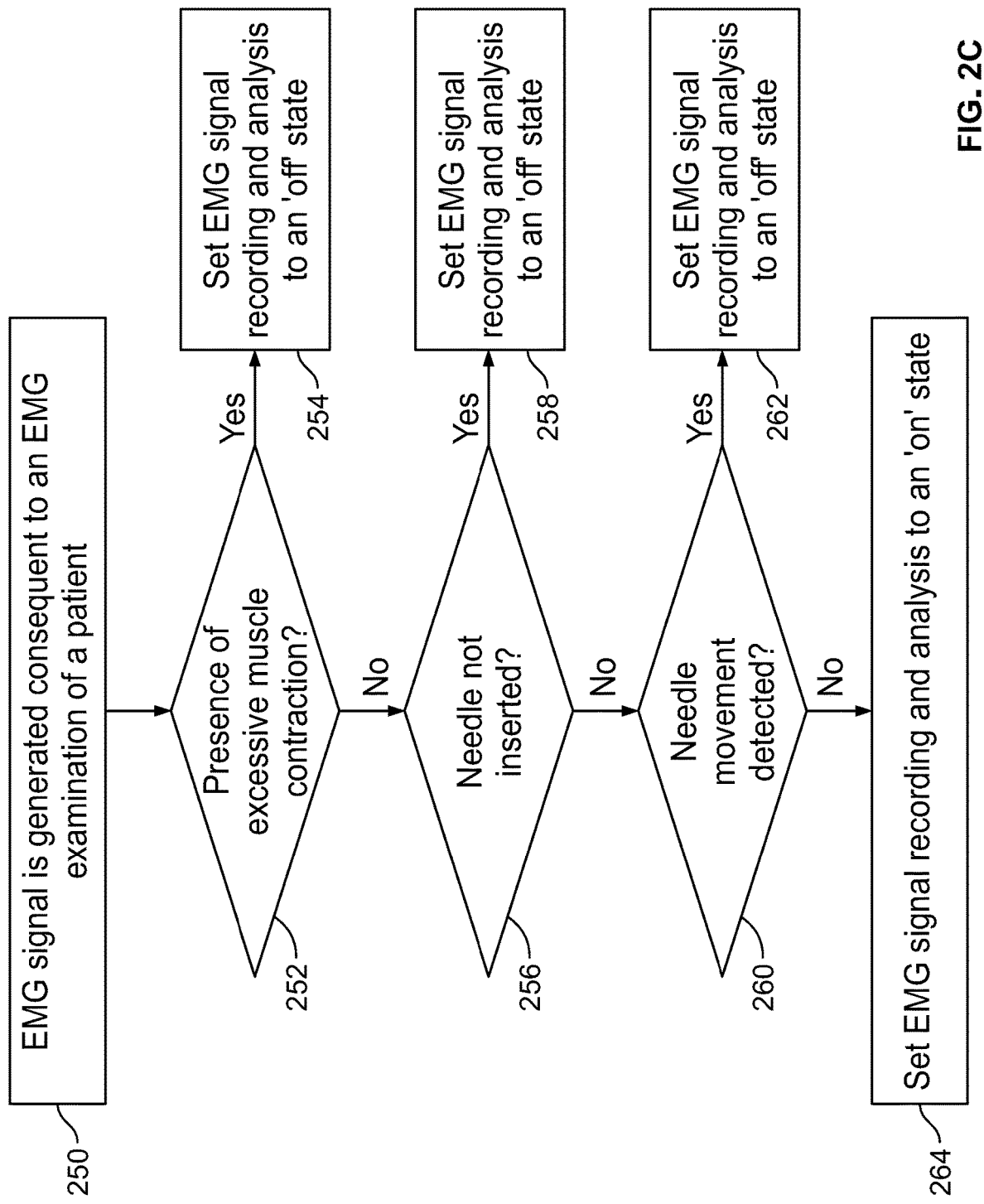
FIG. 2C is a flowchart showing a plurality of steps of a method for detecting artifact EMG signal/data and trigger automatic setting of a state of EMG signal recording and analysis, in accordance with an embodiment of the present specification.

FIG. 2C is a flowchart of a plurality of steps of a method of determining artifact EMG signal/data from actual, non-artifact data to trigger automatic setting of a state of EMG signal recording and analysis, in accordance with an embodiment of the present specification. In embodiments, the method is implemented as a plurality of programmatic instructions carried out by the EMG recording state detection engine or module 105 (FIG. 1).

Referring to FIGS. 1 and 2C, at step 250 EMG signal activity is generated as a result of an operator performing an EMG examination of a patient by using a needle electrode to sample the patient's muscle. At step 252, the generated EMG signal is analyzed by the EMG recording state detection engine 105 to check if the signal is associated with a first artifact, or artifact relating to excessive muscle contraction, as defined above, or 'noisy state' associated with an excessive contraction level of the patient's muscle. In embodiments, excessive contraction level of the muscle is determined by measuring the number of peaks detected per second (PP S) in the signal and comparing the number of PPS against a predefined threshold, wherein each peak detected has a minimum amplitude of 25 µV. In some embodiments, the predefined threshold ranges from 50 to 60 PPS. In one embodiment, the threshold is 50 PPS. In another embodiment the threshold is 55 PPS. In yet another embodiment, the threshold is 60 PPS.

FIG. 2B is an EMG Graphical User Interface (GUI) screen 220 illustrating detection of an artifact signal 225 associated with an excessive muscle contraction, in accordance with an embodiment of the present specification. An indicator 230, such as an intensity bar, displays the signal condition of muscle contraction above the threshold. In some embodiments, the indicator 230 is indicative of the number of PPS that are being measured and how many MUP units are available per second. It should be appreciated that as the muscle contraction force increases the signal 225 tends to get noisier with several motor units firing. This is because a patient's body fires more motor units as the muscle activity increases. In some embodiments, the indicator 230 displays a first color (such as green, for example) when the number of peaks per second are below the threshold and displays a second color (such as red, for example) when the number of peaks per second are above the threshold.

Referring back to FIGS. 1 and 2C, if the detected number of peaks per second in the signal is greater than a threshold value, the signal is determined to be an artifact associated with excessive muscle contraction. Consequently, at step 254, the EMG signal recording and analysis is set to an 'off' state (that is, recording and analysis of the EMG signal is discontinued or stopped). However, if the detected number of peaks per second in the signal is less than or equal to the threshold, the process moves to step 256.

At step 256, the generated EMG signal is analyzed by the EMG recording state detection engine 105 to check if the signal is associated with a second artifact, or artifact relating to needle non-insertion, as defined above, or 'noisy state' associated with the needle not having been inserted in the patient's muscle. In embodiments, the signal associated with 'needle not inserted' is determined by a presence of 'mains' noise or interference above a threshold in relation to the total energy of the signal—that is, signal picked up by the needle from a power line. In some embodiments, the 'mains' noise frequency ranges between 50 and 60 Hz. In one embodiment, the 'mains' noise has a frequency in a range of 50 to 55 Hz. In another embodiment, the 'mains' noise has a frequency in the range of 55 to 60 Hz. In some embodiments, the 'mains' noise is detected by comparing a total power of the generated EMG signal to the power in the range of 50 to 60 Hz. If a presence of 'mains' noise is detected, which in various embodiments, is determined as mains content (signal content having a frequency of 50 Hz-60 Hz) greater than 10% of the total signal, the signal is determined to be an artifact. Consequently, at step 258, the EMG signal recording and analysis is set to an 'off' state. However, if a presence of excess 'mains' noise is not detected then the process moves to step 260.

At step 260, the generated EMG signal is analyzed by the EMG recording state detection engine 105 to check if the signal is associated with a third artifact, or artifact relating to needle movement, as defined above, or 'noisy state' associated with the needle being moved from one site to another in the patient's muscle ('needle movement'). In embodiments, the signal associated with 'needle movement' is determined by the presence of a characteristic waveform comprising infrequent, short duration and high amplitude bursts of activity when the needle is moved, preceded and followed by quiet, substantially low amplitude or activity signals. In some embodiments, the bursts are of a duration of less than 50 milliseconds, have amplitudes typically greater than 500 µV, and frequently saturate the amplifier. In some embodiments, the bursts have a 10 ms duration and amplitude greater than 500 µV. These bursts are relative to a background, or baseline activity, having signals with an average amplitude of less than 50 µV. If a presence of the characteristic waveform is detected, the signal is determined to be an artifact. Consequently, at step 262, the EMG signal recording and analysis is set to an 'off' state. However, if a presence of the characteristic waveform is not detected then the process moves to step 264.

At step 264, the EMG recording state detection engine 105 concludes that the EMG signal is actual, non-artifact and consequently the EMG signal recording and analysis is set to an 'on' state (that is, recording and analysis of the EMG signal is continued or commenced).

It should be appreciated that the order of performing the steps 252, 256 and 260 is only exemplary and that in alternated embodiments these steps may be performed in any other order.

Automatic SFEMG Reference Fiber Selection Module 110

Within a motor unit, there are a plurality of muscle fibers that work together. When performing single fiber electromyography (SFEMG) examination, a needle electrode is inserted into the muscle in such a way that electrical activity from a plurality of muscle fibers belonging to a motor unit is recorded. That is, the motor unit is broken down into its muscle fibers. Thereafter, one of the plurality of muscle fibers is selected as a reference fiber and its synchronization (or jitter) to the other muscle fibers is analyzed and reported. As known to persons of ordinary skill in the art, jitter is a nerve to muscle signal indicating the variation in timing between different muscle fiber activation in the same motor unit, and excess jitter may be a sign that a nerve/muscle junction may not be working properly.

Persons of ordinary skill in the art would appreciate that if electrical activity from more than two muscle fibers is recorded then selecting different fibers as a reference fiber will render different jitter levels and result in a different analysis. Stated differently, the jitter level and associated analysis will differ depending upon the action potential peak of a fiber, from the different fibers, which is selected as the reference. In embodiments, it is desired to select the action potential peak of the fiber that results in the most stable signal or that generates the least artificial instability, wherein artificial instability is defined as signal instability created by artifact or user error, such as moving the needle. Existing EMG machines do not provide any automatic way to manage this situation. Conventionally, in some situations selection, of a reference fiber is performed by the operator manually in a random fashion and in other situations the EMG analysis software selects the fiber with the largest amplitude. In accordance with an aspect of the present specification, the EMG display and analysis software includes an SFEMG reference fiber selection engine or module 110 to automatically determine and select an action potential peak of a reference fiber, from a plurality of muscle fibers in a motor unit, which results in minimum jitter for the plurality of fibers.

Figure 3A:
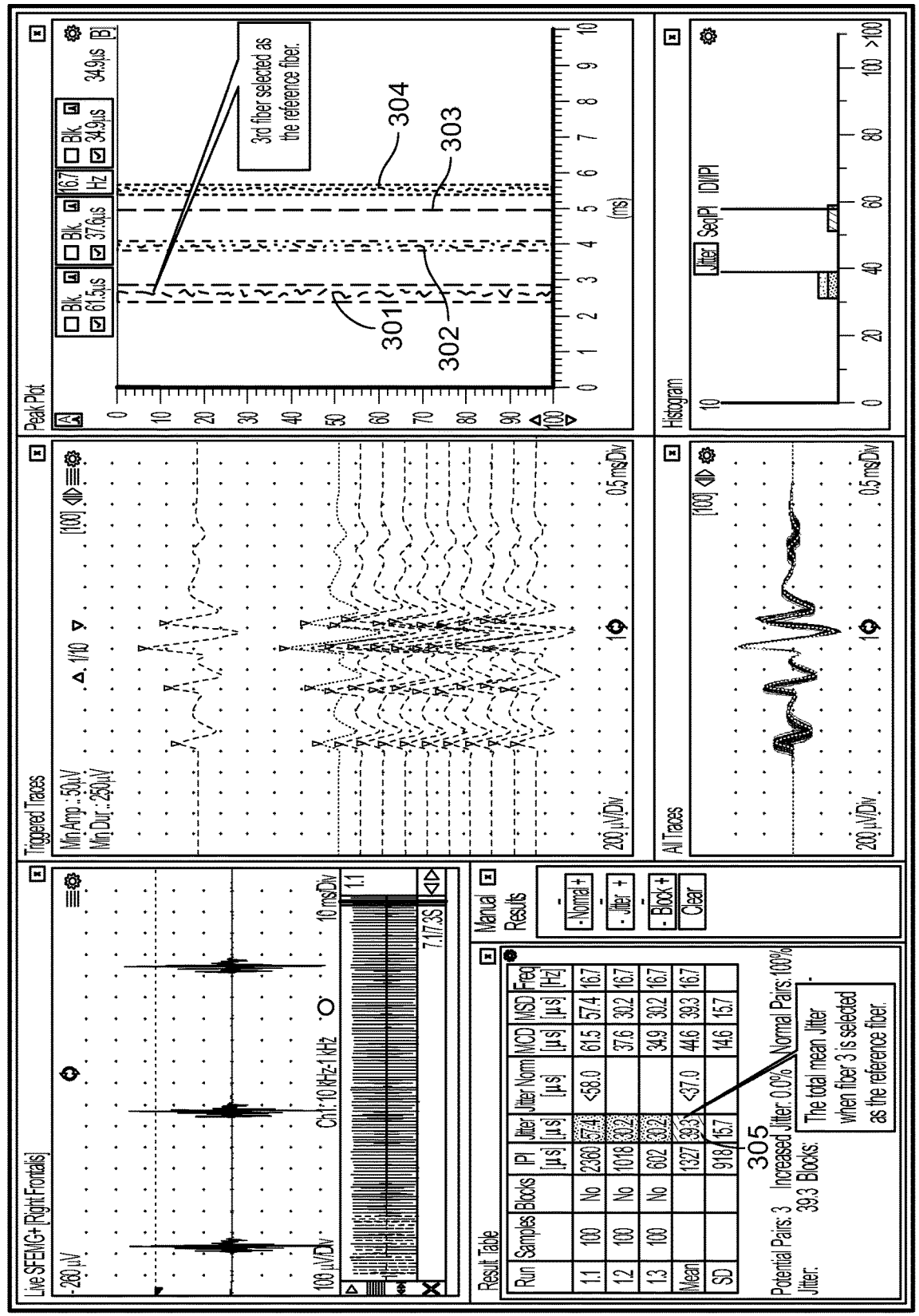
FIG. 3A is an EMG GUI screen illustrating a first total mean jitter calculated by selecting a first reference fiber, in accordance with an embodiment.
Figure 3B:
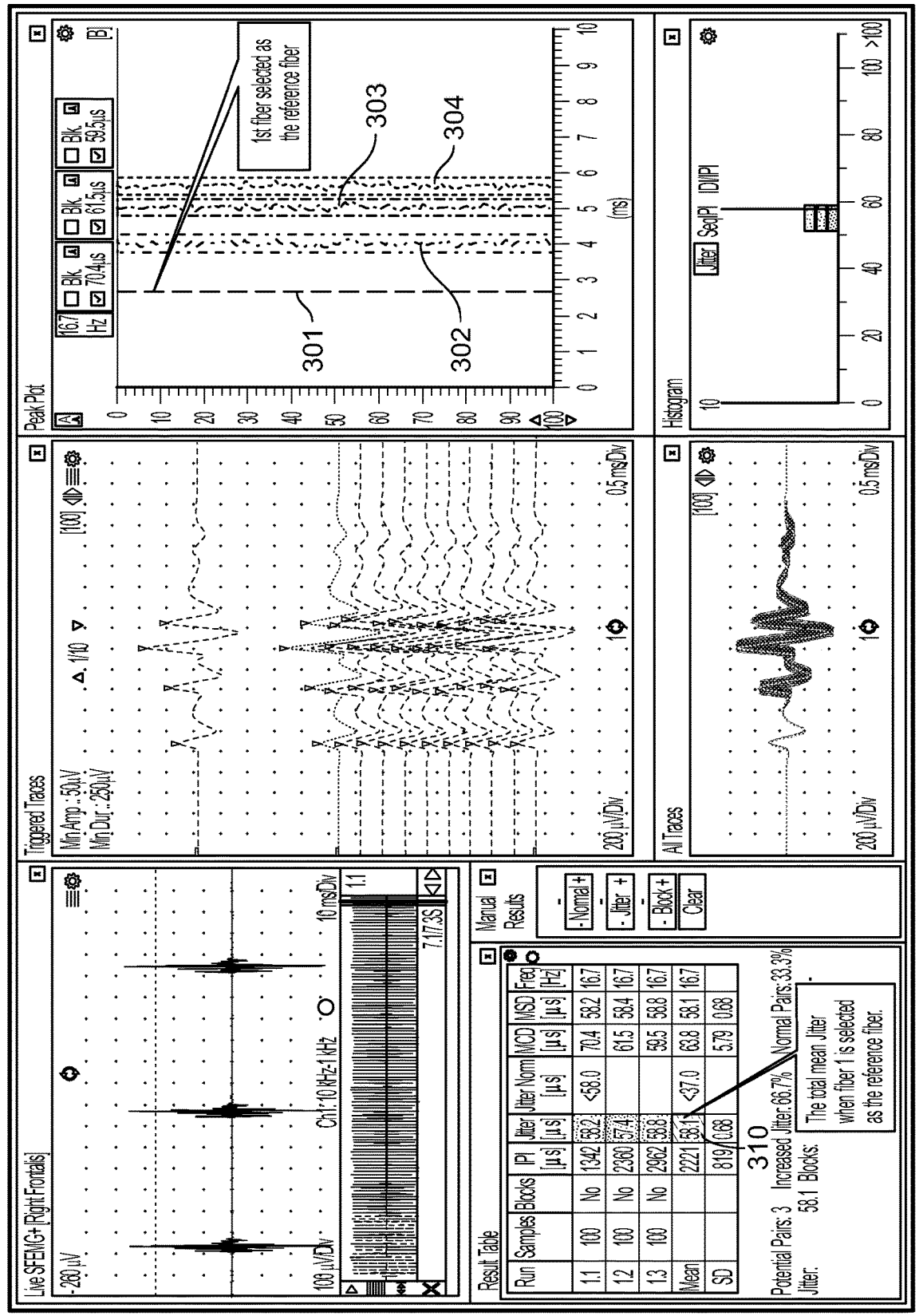
FIG. 3B is the EMG GUI screen of FIG. 3A illustrating a second total mean jitter calculated by selecting a second reference fiber, in accordance with an embodiment.
Figure 3C:
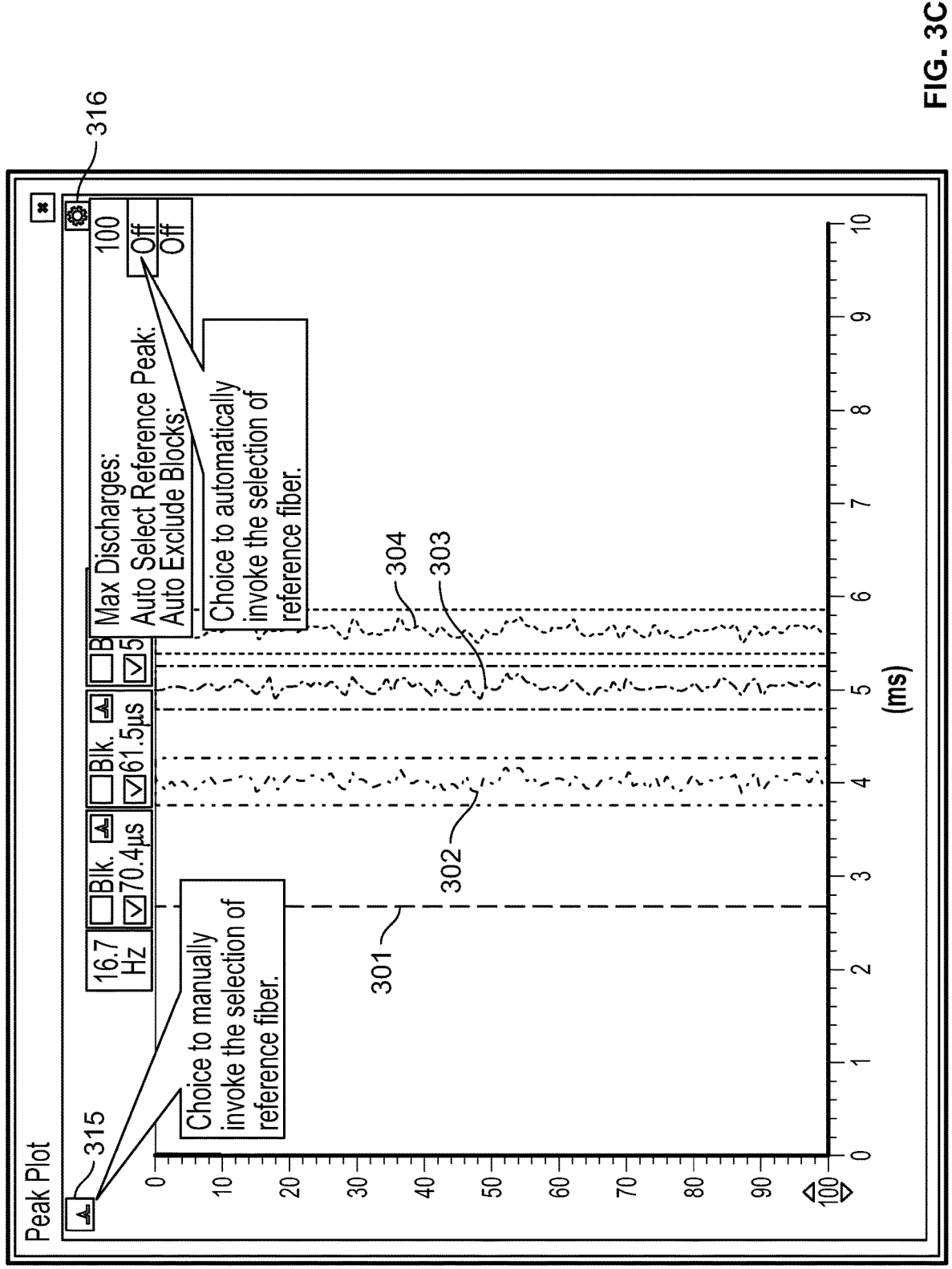
FIG. 3C illustrates a portion of the EMG GUI screen of FIG. 3A for choosing between a manual or an automatic option for reference fiber selection, in accordance with an embodiment.

FIG. 3A is an EMG GUI screen illustrating a first jitter calculated by selecting a first reference fiber. FIG. 3B is the EMG GUI screen illustrating a second jitter calculated by selecting a second reference fiber. FIG. 3C illustrates a portion of the EMG GUI screen for choosing between manual or automatic options for reference fiber selection. As shown in FIG. 3A, EMG activity of four muscle fibers 301, 302, 303 and 304 is recorded in association with stimulation of a single motor unit. Selection of the fiber 303, as a reference fiber, results in a first jitter 305 for the four fibers (in microseconds). As shown in FIG. 3B, selection of another fiber as the reference, that is fiber 301, results in a second jitter 310 (in microseconds). In this exemplary embodiment, the first jitter 305 is less than the second jitter 310. In accordance with an embodiment, the SFEMG reference fiber selection engine 110 automatically selects each of the four fibers 301, 302, 303 and 304 as a reference fiber and automatically calculates the jitter corresponding to each of the selected reference fiber. The reference fiber that generates the least jitter is automatically set as an optimal reference fiber. In embodiments, the SFEMG reference fiber selection engine 110 uses consecutive Inter Potential Interval (IPI) and calculates a mean consecutive difference of the IPI (the MCD) that is presented as jitter. SFEMG is the analysis of the signal from multiple muscle fibers belonging to the same motor unit (innervated by the same nerve/axon). Each muscle fiber is generating an action potential when it is activated and the action potentials are recorded as an EMG signal with multiple peaks representing each muscle fiber. The Inter Potential Interval (WI) is defined as the duration/distance between two such peaks. The mean consecutive difference (MCP) of the IPI is defined as the average difference between consecutive IPIs.

As shown in FIG. 3C, a first indicator 315 can be selected to enable manual selection of the reference fiber while a second indicator 316 can be selected to enable automatic selection of the reference fiber using the SFEMG reference fiber selection engine 110 of the present specification. In various embodiments, the indicators 315, 316 may be icons or buttons.

Figure 3D:
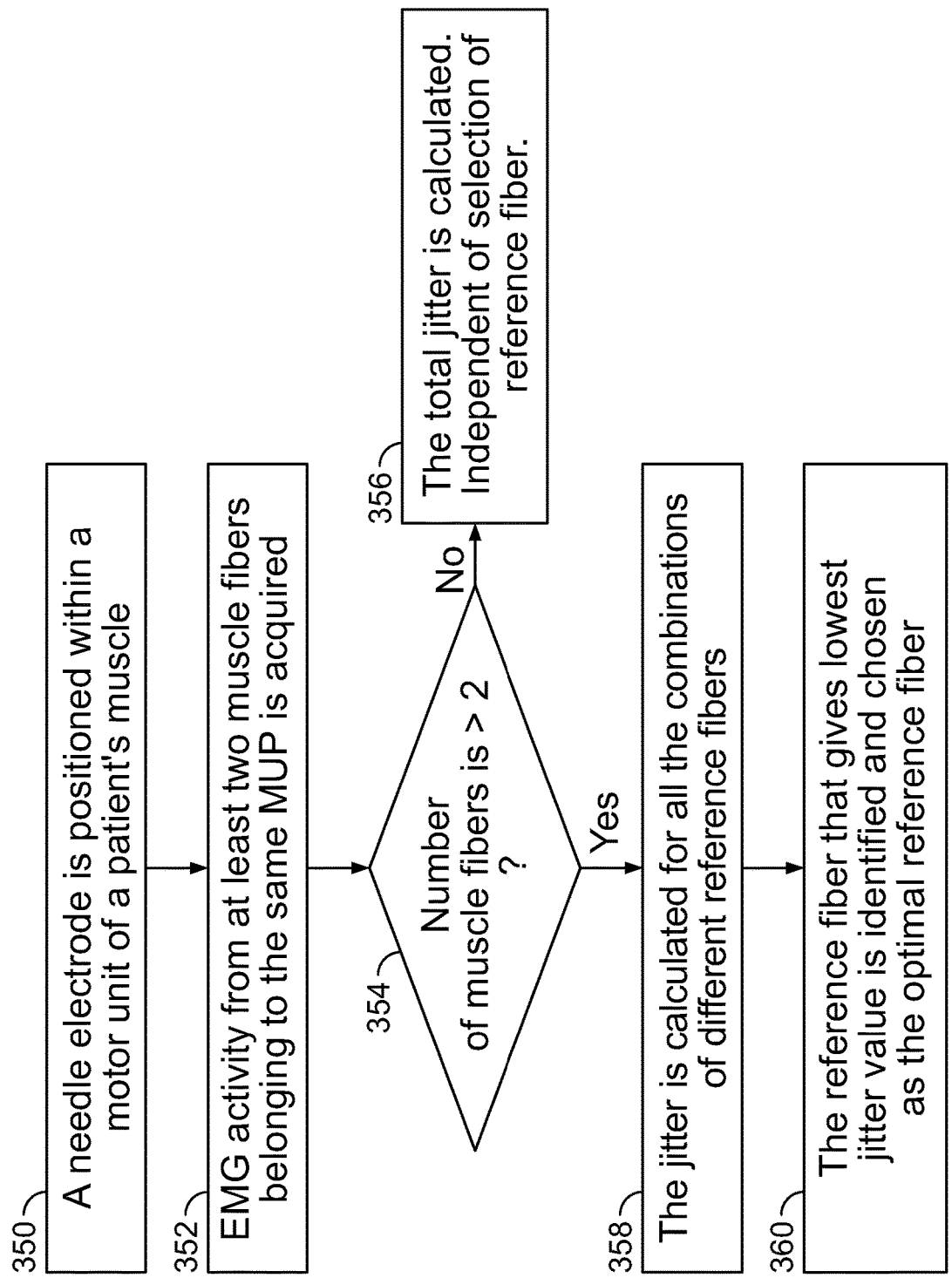
FIG. 3D is a flowchart showing a plurality of steps of a method for automatically determining and selecting an optimal reference fiber when EMG activity from more than two fibers is recorded at the same time, in accordance with an embodiment.

FIG. 3D is a flowchart of a plurality of steps of a method to automatically determine and select an optimal reference fiber when EMG activity (or action potentials) from more than two fibers is recorded at the same time, in accordance with an embodiment. In embodiments, the method is implemented as a plurality of programmatic instructions carried out by the SFEMG reference fiber selection engine 110 (of FIG. 1). Referring to FIG. 3D, at step 350 a needle electrode is positioned within a motor unit of a patient's muscle, wherein the motor unit is in neuronal communication with a plurality of muscle fibers. At step 352, EMG activity from the plurality of muscle fibers is acquired and recorded. At step 354, a determination is made whether the number of muscle fibers, generating the EMG activity simultaneously, is greater than two fibers. If the number of muscle fibers comprise only two fibers then, at step 356, any one of the two fibers is selected as a reference fiber and total jitter is calculated for the two fibers, independent of the selection of a reference fiber. In case of a single fiber, jitter calculation is not required.

However, if, at step 354, EMG activity is detected for more than two muscle fibers then, at step 358, any one of the fibers is selected as the reference fiber and total jitter is calculated for the more than two fibers. Step 358 is repeated or iterated by selecting each fiber, of the more than two fibers, as the reference fiber and calculating the total jitter with respect to that reference fiber. At step 360, the reference fiber that gives the lowest or minimum jitter value is identified and is chosen, either manually or automatically, as the optimal reference fiber for further analyses.

Automatic EMG Trigger Module 115

While performing an EMG examination a needle is inserted into a muscle to record and display the muscle's electrical activity. The EMG examination is directed towards evaluating the properties of individual motor units as they occur in real time in the ongoing muscle activity. The EMG is typically displayed by the EMG machine both as a continuous signal referred to as "Live EMG" as well as a time locked signal referred to as "Triggered EMG". The function of time-locking is referred to as triggering and can be performed in a plurality of ways as would be evident to persons of ordinary skill in the art. The Live EMG provides information about the interaction between different motor units while the Triggered EMG is used to assess information about a single motor unit.

An embodiment of a triggering process, also referred to as Level Triggering, comprises an operator setting a first trigger level amplitude for a Live EMG signal, wherein any portion of the Live EMG signal that meets or exceeds the first trigger level amplitude is captured and displayed as Triggered EMG. In alternate embodiments, the Level Triggering process may be configured to trigger a portion of the Live EMG that falls below the first trigger level amplitude. Trigger level amplitude, such as the first trigger level amplitude, is set to capture or freeze a reoccurring signal that is typically a MUP and can be either normal or pathological. Thus, setting of a trigger level amplitude enables capturing a signal activity to analyze the amplitude, duration and frequency of the signal activity.

If there is a reoccurring signal in the Live EMG of a second amplitude, and the second amplitude is higher than the first trigger level amplitude that was set (such that the first trigger level amplitude is just below the second amplitude), this will result in different instances of that specific reoccurring signal to be captured and displayed beneath each other in a "time-locked" fashion in a triggered EMG window thereby convoluting an analysis.

In accordance with an aspect of the present specification, the EMG display and analysis software includes an automatic EMG trigger engine or module 115 that continuously analyzes an incoming EMG signal and automatically adjusts the trigger level to facilitate a display of triggered motor unit data without the need for any manual intervention by the operator—thereby fostering a hands-free approach towards using the EMG machine. Consequently, the operator may focus on keeping the patient engaged or distracted instead of devoting too much time on manually operating the EMG machine. Persons of ordinary skill in the art would appreciate that while the present specification describes automation of a Level Triggering process, this should in no way be considered limiting and that in other embodiments the EMG trigger engine may be configured to automate a 'Window Trigger' process that triggers a portion of the Live EMG that is above a first trigger value but that needs to reach its peak below a second trigger value.

Figure 4A:
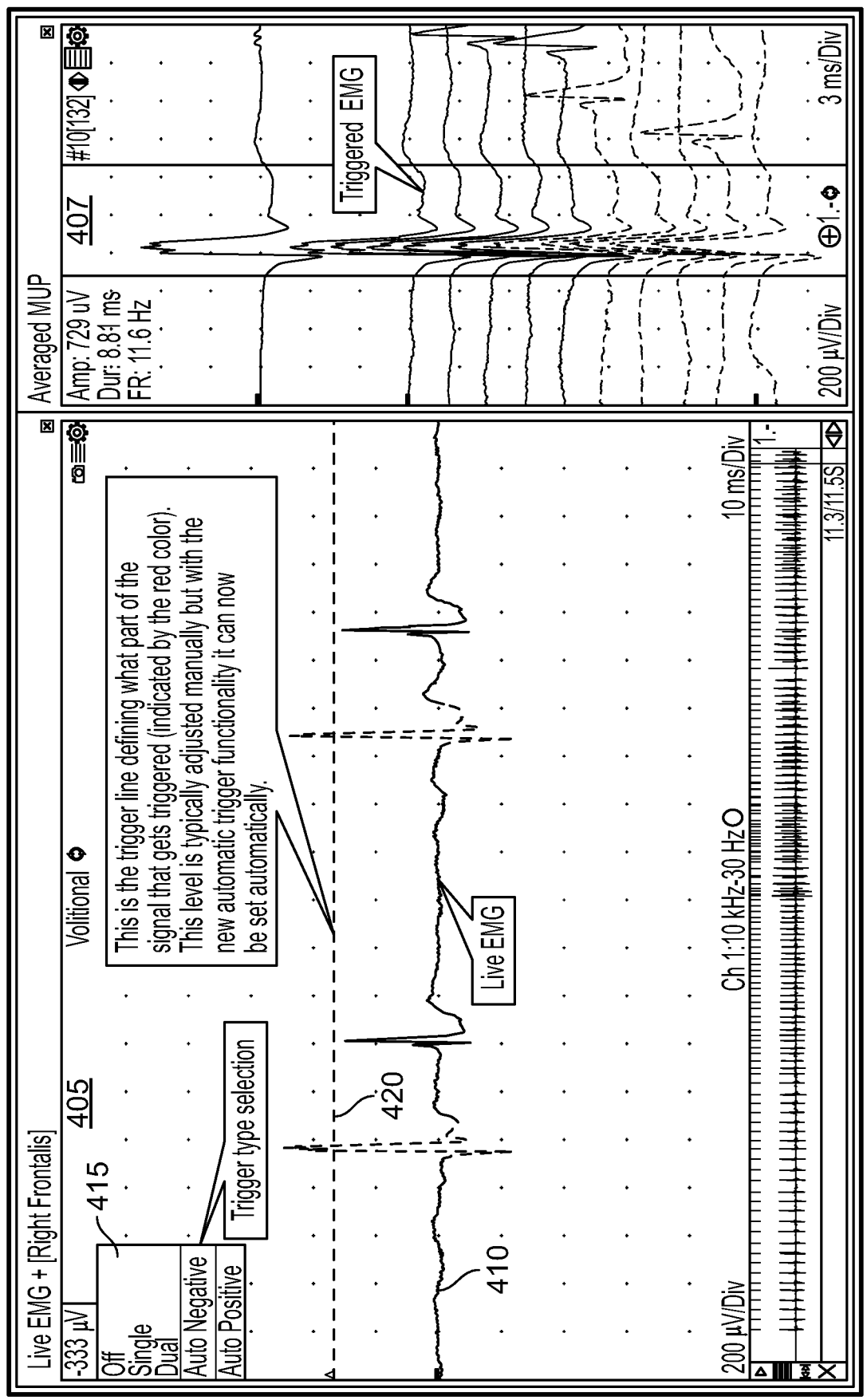
FIG. 4A is an EMG GUI screen illustrating automatically setting a triggering level, in accordance with an embodiment of the present specification.

FIG. 4A is an EMG GUI screen illustrating automatic setting of triggering level, in accordance with an embodiment of the present specification. As shown, the first window 405 displays a Live EMG waveform 410. An indicator 415, such as an icon or button, when selected allows an operator to enable automatic setting of a trigger level depending on the nature of the waveform 410, such as whether the waveform 410 is positive or negative. The window 405 illustrates a line 420 indicative of a trigger level automatically set by the EMG trigger engine or module 115. As a result, window 407 displays triggered EMG including waveforms with amplitudes above the trigger level (line 420). The operator may, alternatively, interact with the indicator 415 to disable automatic setting of the trigger level.

Figure 4B:
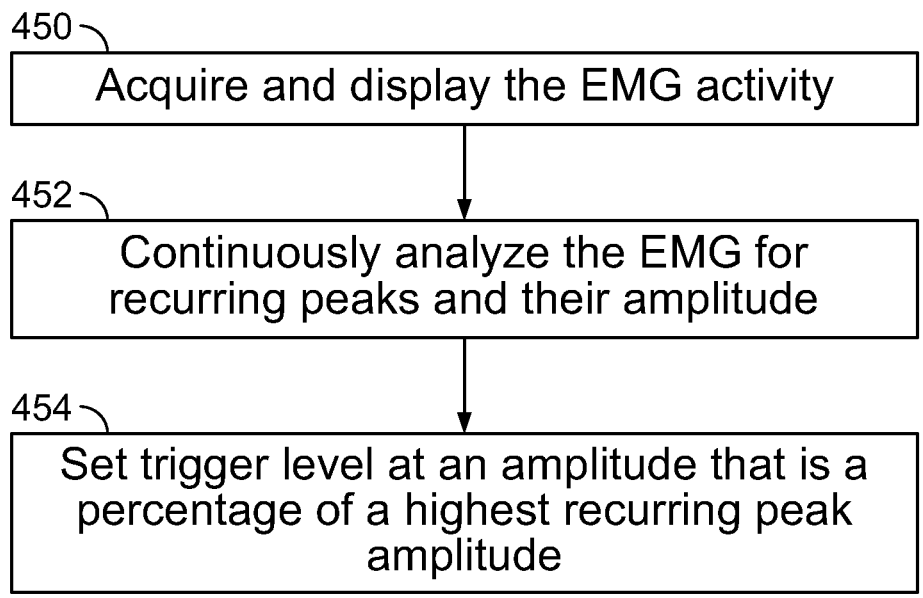
FIG. 4B is a flowchart of a plurality of steps showing a method for automatically modulating a trigger level with reference to a Live EMG signal, in accordance with an embodiment of the present specification.

FIG. 4B is a flowchart of a plurality of steps of automatically modulating a trigger level with reference to a Live EMG signal, in accordance with an embodiment of the present specification. In embodiments, the method is implemented as a plurality of instructions by the automatic EMG trigger engine or module 115 of the present specification.

Referring to FIG. 4B, at step 450 an operator performs an electromyography (EMG) examination, using a needle electrode to acquire and display the electrical activity from a muscle and generate Live EMG signal data. At step 452, the EMG signal is continuously analyzed to detect recurring peaks and their amplitudes. An algorithm of the automatic EMG trigger module 115 analyzes the runtime data for maximum peaks and distribution of peaks to automatically detect or set a trigger baseline. In some embodiments, the algorithm of the automatic EMG trigger module 115 continuously analyzes to the last 0.5 seconds of EMG signal for peaks and turns to set a trigger baseline. That is, the EMG signal is continuously analyzed to detect maximum peaks and distributional peaks (how peaks are distributed along the signal) and determine where the turns and peaks are dispersed and a distribution of amplitudes. A turn is defined as anytime the signals turns from negative to positive or positive to negative. In embodiments, the peaks may be positive or negative. In some embodiments, the change in signal direction must have a total amplitude change of at least 25 µV to constitute a turn.

At step 454, a trigger level is automatically set, modulated or adjusted to a predetermined fraction or percentage of a highest or maximal recurring peak amplitude (from the detected recurring peaks, of step 452), to trigger and evaluate a motor unit. In some embodiments, the trigger level is set at an amplitude that is within a predefined percentage of the highest or maximum recurring peak amplitude. In one embodiment, the trigger level is set at an amplitude that is within a range of 50% to 95% of the highest or maximum recurring peak amplitude, preferably 70% to 90%, and more preferably 80% to 85%, and every numerical increment therein. In other words, automated setting and modulation of the trigger level enables portions of the EMG signal having high amplitude and occurring frequently to be accentuated.

In embodiments, the trigger level setting, adjustment or modulation is done with a "time lag" averaged over time to avoid single large peaks causing big movements in the trigger level. More specifically, a plurality of trigger level values are first obtained over a predefined time period. Those trigger level values are then averaged. If the new average trigger level value, obtained over the predefined period of time, varies from the previously set trigger level value by more than a predefined amount, then the trigger level value of the system will be modified to the new average trigger level value.

Because different motor units have different amplitudes, steps 452 and 454 may be repeated for Live EMG signals corresponding to each motor unit stimulated or triggered by the needle electrode at different sites of a patient's muscle. This enables automatic modulation of the trigger level with reference to the motor unit being stimulated or triggered.

EMG Motor Unit Recruitment Ratio and Recruitment Frequency Analyzer (EMG MU RR and RF Analyzer) Module 120

Disease weakens a patient's muscles and the motor units also become weaker and, as a result, more motor units are needed to activate the muscles. In embodiments, an EMG examination is directed towards evaluating the relation between muscle force and the properties of recorded motor unit potential trains through parameters such as recruitment ratio and frequency. Muscle force is modulated by increasing or reducing the frequency of firing of a motor unit and the number of motor units that are activated simultaneously. The recruitment ratio and frequency parameters are conventionally estimated manually from looking and listening to the EMG signal while the contraction level of the muscle varies, which requires extensive experience and is difficult to quantify. As persons of ordinary skill in the art would be aware, operators or physicians conventionally rely on listening to the EMG signal and from the sound make a subjective guess if the recruitment of motor units is normal or represents a degree of pathology.

In accordance with an aspect of the present specification, the EMG display and analysis software includes an EMG motor unit recruitment ratio and frequency analyzer engine or module 120 that triggers automatic calculation and display of the recruitment ratio and recruitment frequency as a consequence of detected, recorded and decomposed motor unit trains.

Figure 5A:
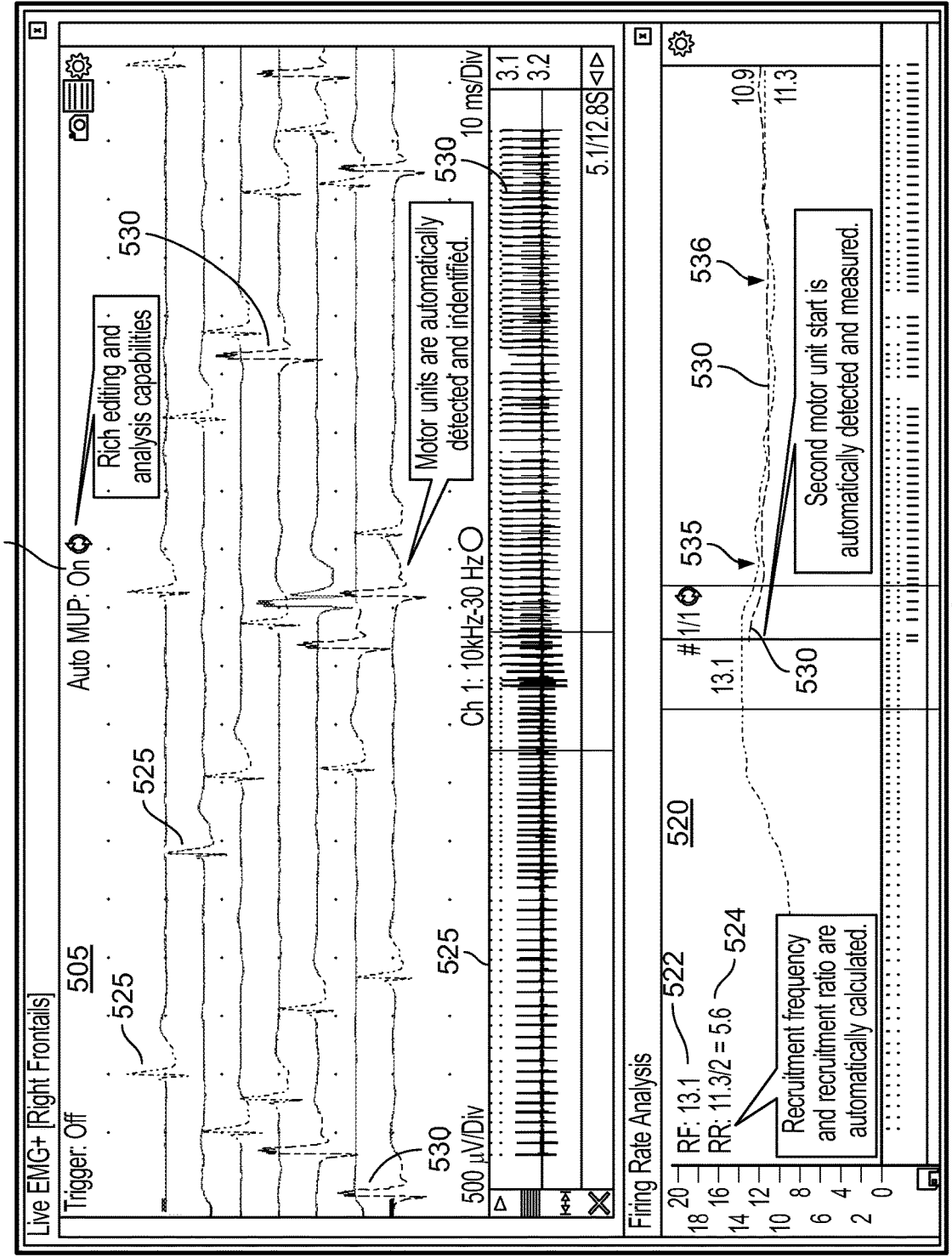
FIG. 5A is an EMG GUI screen illustrating detection of motor units for automatically determining and displaying associated firing parameters, in accordance with an embodiment of the present specification.

FIG. 5A is an EMG GUI screen illustrating detection of motor units for subsequent automatic determination and display of associated firing patterns and parameters, in accordance with an embodiment of the present specification. As shown, window 505 illustrates automatic detection and display of Live EMG activity or waveform of a first motor unit 525 firing at a first frequency. The first frequency changes over time until eventually a second motor unit 530 is recruited, wherein the second motor unit 530 fires at a second frequency. In an embodiment, the first waveform 525 is displayed in a first color (such as green, for example) and the second waveform is displayed in a second color (such as orange, for example). Since the waveforms 525, 530 represent actual, non-artifact biologic EMG data, the EMG recording state detection engine 105 of FIG. 1 automatically sets the EMG display and analysis to an 'on' state 515. Also, a window 520 illustrates automatically calculated values 522, 524 for the recruitment ratio and recruitment frequency parameters, respectively, corresponding to the first and second motor units 525, 530. In one embodiment, the system only calculates the recruitment ratio and recruitment frequency parameters for waveforms that represent actual, non-artifact biologic EMG data. The window 520 also illustrates, in the form of graphs 535, 536, automatic detection and measurement of the start of the second motor unit 530 at the detected recruitment frequency 522 of the first motor unit 525. The graphs 535, 536 present a change in frequencies of firing, over time, of each motor unit 525, 530.

Figure 5B:
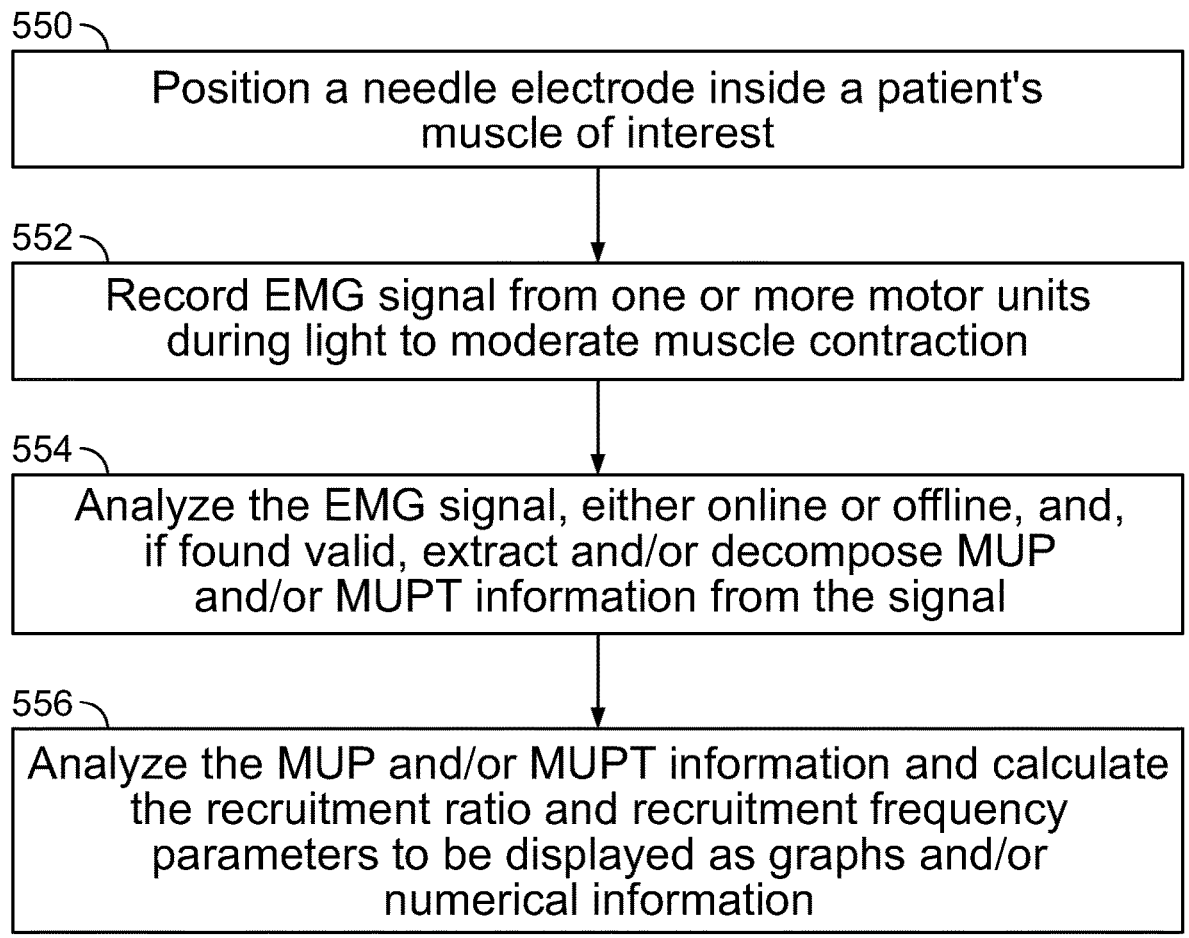
FIG. 5B is a flowchart showing a plurality of steps of a method for automatically calculating a recruitment ratio and recruitment frequency associated with a plurality of motor units, in accordance with an embodiment of the present specification.

FIG. 5B is a flowchart of a plurality of steps of a method of automatically calculating the recruitment ratio and recruitment frequency associated with a plurality of motor units, in accordance with an embodiment of the present specification. In embodiments, the method is implemented as a plurality of instructions by the EMG motor unit recruitment ratio and frequency analyzer engine or module 120 of the present specification.

Referring to FIG. 5B, at step 550 a needle electrode is positioned within a patient's muscle of interest. At step 552, EMG signal or activity from one or more motor units is recorded during light to moderate contraction of the muscle. At step 554, the EMG signal is analyzed, such as (for example) by the EMG Recording State Detection engine or module 105, to determine if the EMG signal is actual, non-artifact/valid biologic activity. If the EMG signal is valid, then MUP and MUPT information is extracted or decomposed from the signal. It should be appreciated that the EMG signal may be analyzed in real-time or offline—that is, from a recorded signal.

Finally, at step 556, the MUP and MUPT information is analyzed and firing parameters, that is the Recruitment Ratio and Frequency parameters are calculated and displayed as graphs and/or numerical information on at least one graphical user interface rendered on a display.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method of using an electromyography device to automatically set a recordation and/or analytical state of a motor unit, the method comprising:
   using the electromyography device, generating an EMG signal from a needle electrode positioned in the patient's muscle tissues;
   using the electromyography device, identifying a presence of a predefined waveform in the EMG signal, wherein the predefined waveform comprises a first portion having a first amplitude and a first frequency and a second portion having a second amplitude and a second frequency, wherein the first amplitude is greater than the second amplitude, wherein the first frequency is greater than the second frequency, and wherein the second portion precedes or follows the first portion;
   using the electromyography device, determining if the identified predefined waveform in the EMG signal corresponds to one of a plurality of predefined artifacts, wherein a first one of the plurality of predefined artifacts is associated with a movement of the needle electrode from a first site to a second site in the muscle tissues;
   using the electromyography device, automatically setting the recordation and/or analytical state to a first status if the EMG signal is determined to be at least one of the plurality of predefined artifacts;
   using the electromyography device, automatically setting the recordation and/or analytical state to a second status if the EMG signal is determined to not be one of the plurality of predefined artifacts; and.

2. The method of claim 1, wherein the first status corresponds to stopping the recordation or analysis of the EMG signal corresponding to the motor unit and wherein the second status corresponds to recording or analyzing the EMG signal corresponding to the motor unit.

3. The method of claim 1, further comprising using the electromyography device to identify an excessive contraction of the muscle tissues based on whether a number of peaks per second detected in the EMG signal is greater than a threshold number of peaks per second, wherein a second one of the plurality of predefined artifacts is associated with the excessive contraction of the muscle tissues.

4. The method of claim 3, wherein the threshold number of peaks per second ranges between 50 and 60 peaks per second.

5. The method of claim 1, further comprising using the electromyography device to identify a second one of the plurality of predefined artifacts based on whether the EMG signal comprises a mains noise frequency.

6. The method of claim 5, wherein the mains noise frequency is in a range from at least one of 50 Hz to 55 Hz or 55 Hz to 65 Hz.

7. The method of claim 1, wherein a second one of the plurality of predefined artifacts is associated with the needle electrode not being properly inserted into the muscle tissues.

8. The method of claim 1, wherein the first portion defines a burst having a duration of less than 50 milliseconds.

9. The method of claim 1, wherein the first amplitude has an amplitude of greater than 500 μV.

10. An electromyography device having a non-transient memory and a processor configured to execute a plurality of programmatic instructions stored in the non-transient memory, wherein, upon execution of the plurality of programmatic instructions, the electromyography device:
    generates an EMG signal while sampling a patient's muscle tissues via a needle electrode;
    identifies a presence of a predefined waveform in the EMG signal, wherein the predefined waveform comprises a first portion having a first amplitude and a first frequency and a second portion having a second amplitude and a second frequency, wherein the first amplitude is greater than the second amplitude, wherein the first frequency is greater than the second frequency, and wherein the second portion precedes or follows the first portion
    determines if the identified predefined waveform in the EMG signal corresponds to one of a plurality of predefined artifacts, wherein a first one of the plurality of predefined artifacts is associated with a movement of the needle electrode from a first site to a second site in the muscle tissues;
    automatically sets a recordation and/or analytical state to a first status if the EMG signal is determined to be at least one of the plurality of predefined artifacts;
    automatically sets the recordation and/or analytical state to a second status if the EMG signal is determined to not be one of the plurality of predefined artifacts; and.

11. The electromyography device of claim 10, wherein the first status corresponds to stopping the recordation or analysis of the EMG signal and wherein the second status corresponds to recording or analyzing the EMG signal.

12. The electromyography device of claim 10, wherein the electromyograph device is further configured to identify an excessive contraction of the muscle tissues based on whether a number of peaks per second detected in the EMG signal is greater than a threshold number of peaks per second, wherein a second one of the plurality of predefined artifacts is associated with the excessive contraction of the muscle tissues.

13. The electromyography device of claim 12, wherein the threshold number of peaks per second ranges between 50 and 60 peaks per second.

14. The electromyography device of claim 10, wherein the electromyograph device is further configured to identify a second one of the plurality of predefined artifacts based on whether the EMG signal comprises a mains noise frequency.

15. The electromyography device of claim 14, wherein the mains noise frequency is in a range from at least one of 50 Hz to 55 Hz or 55 Hz to 65 Hz.

16. The electromyography device of claim 10, wherein a second one of the plurality of predefined artifacts is associated with the needle electrode not being properly inserted into the muscle tissues.

17. The electromyography device of claim 10, wherein the first portion defines a burst having a duration of less than 50 milliseconds.

* * * * *